United States Patent
Noma et al.

(10) Patent No.: US 8,983,035 B2
(45) Date of Patent: Mar. 17, 2015

(54) RADIOGRAPHIC IMAGE DETECTOR AND CONTROLLING METHOD THEREFOR

(71) Applicant: FUJIFILM Corporation, Tokyo (JP)

(72) Inventors: Kentaro Noma, Ashigarakami-gun (JP); Kenji Nakamura, Ashigarakami-gun (JP); Naoto Iwakiri, Ashigarakami-gun (JP); Kouichi Kitano, Ashigarakami-gun (JP); Keita Watanabe, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 290 days.

(21) Appl. No.: 13/683,428

(22) Filed: Nov. 21, 2012

(65) Prior Publication Data
US 2013/0136234 A1  May 30, 2013

(30) Foreign Application Priority Data

Nov. 25, 2011 (JP) .................................. 2011-257996
Nov. 9, 2012 (JP) .................................. 2012-247525

(51) Int. Cl.
*G01T 1/24* (2006.01)
*G01T 1/16* (2006.01)
(Continued)

(52) U.S. Cl.
CPC ...... *H05G 1/64* (2013.01); *G01T 1/171* (2013.01); *H04N 5/32* (2013.01); *A61B 6/548* (2013.01)
USPC ............ 378/97; 378/98.8; 378/189; 378/91; 378/109; 378/114; 250/370.09; 250/370.08; 250/214 DC; 250/370.07; 250/584

(58) Field of Classification Search
CPC ......... H04N 5/32; H04N 5/374; H04N 5/353; H04N 5/232; H04N 5/378; H04N 5/361; H04N 5/3655; H04N 5/3658; H04N 5/30; H04N 5/357; G01T 1/2018; G01T 1/16; G01T 1/17; G01T 1/24; G01T 1/247; G01T 1/2928; G01T 1/026; G01T 1/20; G01T 1/244; G01T 1/246; G01T 1/2964
USPC ............... 250/370.09, 370.08, 366, 371, 394, 250/205, 208.1, 214 P, 338.4, 363.01, 250/370.07, 370.11, 395, 580, 585, 591; 378/98.8, 109, 114, 169, 116, 182, 378/189, 91, 97

See application file for complete search history.

(56) References Cited

U.S. PATENT DOCUMENTS 2,885,563 A * 5/1959 Batina et al. ................... 250/205
3,491,239 A * 1/1970 Dalman .......................... 378/97

(Continued)

*Primary Examiner* — David A Vanore
(74) *Attorney, Agent, or Firm* — Birch, Stewart, Kolasch & Birch, LLP

(57) ABSTRACT

A flat panel detector has pixels for obtaining image signals and detective pixels for detecting the amount of incident x-rays. A signal processing circuit is of a pipeline-type, wherein first and second buffer memories are connected to the output of an A/D converter. In a dose detecting operation, the signal processing circuit repeats primary cycles alternately with secondary cycles of a shorter length than the primary cycles. In the primary cycle, a dose detection signal based on electric charges from the detective pixels is input in the first buffer memory and, simultaneously, a dummy signal is output from the second buffer memory. In secondary cycle, the dose detection signal is output from the first buffer memory and, simultaneously, a second dummy signal is input in the second buffer memory. On the basis of the dose detection signals, a start-of-radiation detector detects the start of x-ray radiation.

20 Claims, 16 Drawing Sheets

(51) Int. Cl.
  *H01L 27/146*  (2006.01)
  *H05G 1/64*  (2006.01)
  *G01T 1/17*  (2006.01)
  *H04N 5/32*  (2006.01)
  *A61B 6/00*  (2006.01)

(56) References Cited

U.S. PATENT DOCUMENTS

| | | | |
|---|---|---|---|
| 6,310,358 B1 * | 10/2001 | Zur | 250/591 |
| 6,326,625 B1 * | 12/2001 | Zur | 250/370.09 |
| 6,696,687 B1 * | 2/2004 | Tomisaki et al. | 250/370.09 |
| 6,950,131 B1 * | 9/2005 | Kleinhans et al. | 348/241 |
| 7,005,663 B2 * | 2/2006 | Maolinbay et al. | 250/584 |
| 7,122,802 B2 | 10/2006 | Petrick et al. | |
| 7,154,548 B2 * | 12/2006 | Liu | 348/302 |
| 8,237,127 B2 * | 8/2012 | Yoshida et al. | 250/370.09 |
| 8,431,905 B2 * | 4/2013 | Kondou | 250/370.08 |
| 8,446,495 B2 * | 5/2013 | Mochizuki et al. | 348/241 |
| 8,476,597 B2 * | 7/2013 | Kuwabara | 250/370.08 |
| 8,536,534 B2 * | 9/2013 | Okada | 250/370.08 |
| 8,633,447 B2 * | 1/2014 | Watanabe | 250/370.09 |
| 8,750,455 B2 * | 6/2014 | Kondou | 378/98.8 |
| 8,759,782 B2 * | 6/2014 | Okada | 250/370.08 |
| 8,866,101 B1 * | 10/2014 | Watanabe et al. | 250/394 |
| 8,872,118 B2 * | 10/2014 | Nishino et al. | 250/370.09 |
| 2002/0100862 A1 * | 8/2002 | Liu | 250/208.1 |
| 2011/0180717 A1 | 7/2011 | Okada | |
| 2012/0199751 A1 * | 8/2012 | Watanabe | 250/370.09 |
| 2012/0201357 A1 * | 8/2012 | Watanabe et al. | 378/114 |
| 2012/0273687 A1 * | 11/2012 | Nariyuki et al. | 250/366 |
| 2013/0136234 A1 * | 5/2013 | Noma et al. | 378/91 |
| 2014/0008523 A1 * | 1/2014 | Okada | 250/208.1 |
| 2014/0061492 A1 * | 3/2014 | Sato et al. | 250/393 |
| 2014/0110595 A1 * | 4/2014 | Iwakiri et al. | 250/394 |
| 2014/0185764 A1 * | 7/2014 | Takenaka et al. | 378/62 |
| 2014/0231658 A1 * | 8/2014 | Kondou | 250/370.09 |
| 2014/0263952 A1 * | 9/2014 | Taghibakhsh et al. | 250/208.1 |
| 2014/0270092 A1 * | 9/2014 | Ogura et al. | 378/189 |
| 2014/0284491 A1 * | 9/2014 | Sato et al. | 250/393 |
| 2014/0291533 A1 * | 10/2014 | Oda | 250/370.07 |
| 2014/0291541 A1 * | 10/2014 | Watanabe et al. | 250/394 |

* cited by examiner

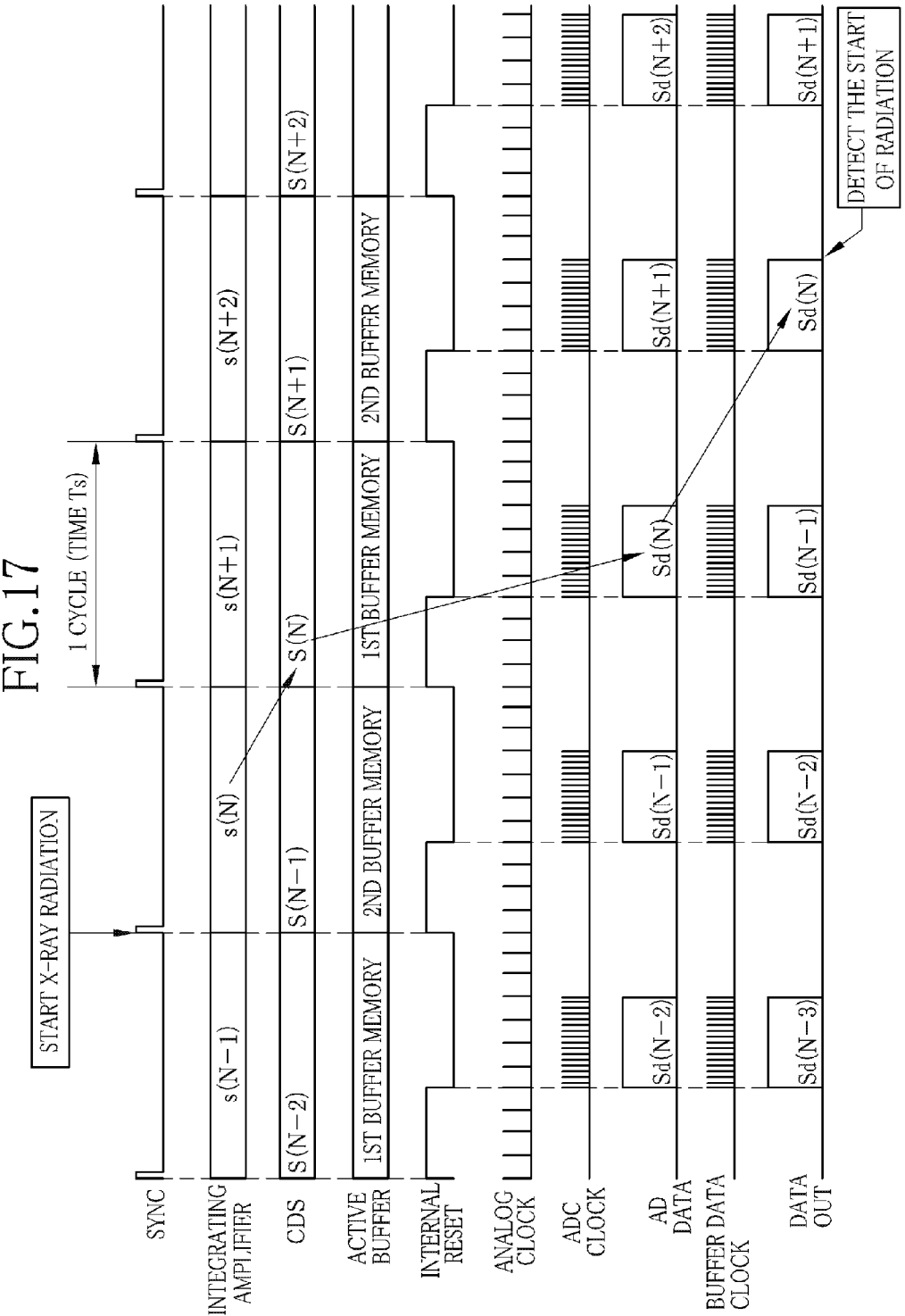

RADIOGRAPHIC IMAGE DETECTOR AND CONTROLLING METHOD THEREFOR

BACKGROUND OF THE INVENTION

1. Field of the Invention

The present invention relates to a radiographic image detector and a method for controlling the radiographic image detector.

2. Description of the Related Art

In the medical field, radiography systems utilizing radioactive rays, such as x-rays, for imaging are widely known. An x-ray radiography system, an example of radiography systems, includes an x-ray projector for projecting x-rays toward a subject or patient and an x-ray imaging apparatus for acquiring a radiograph or x-ray image of the subject from the x-rays that have penetrated the subject. The x-ray projector includes an x-ray source, a source controller unit for controlling the x-ray source, and an activation switch for inputting a command for actuating the x-ray source to the source controller. The x-ray imaging apparatus includes an x-ray image detector for detecting an x-ray image or x-ray images from incident x-rays, and a console for controlling operation of the x-ray image detector, storing and displaying the x-ray images.

X-ray image detectors using a flat panel detector (FPD) as an imaging device have recently been widely spread. The FPD has an imaging area in which an array of pixels are provided for accumulating signal charges corresponding to x-rays that are incident on the respective pixels. Each pixel includes a photoelectric conversion element for generating and accumulating the charges and a switching element, such as a thin film transistor (TFT). In the FPD, the accumulated signal charges are read out from the photoelectric conversion elements of the pixels line by line of the pixel array when the switching elements are turned on, and are fed through signal lines, which are provided one for each column of the pixel array, to a signal processing circuit. In the signal processing circuit, the signal charges are converted to a voltage signal, electrically detecting an x-ray image of the subject.

The signal processing circuit is provided with integrating amplifiers, correlated double sampling (CDS) circuits, A/D converters and etc. The integration amplifiers are individually provided on each signal line that is connected to respective pixels of one column, so that each integration amplifier integrates the signal charges from the signal line to convert the signal charges to an analog voltage signal. The CDS circuits are also provided for the individual signal lines, being connected to respective output terminals of the integration amplifiers. The CDS circuit includes a sample-and-hold circuit, which renders the analog voltage signal from the integration amplifier with correlated double sampling for noise reduction, and holds the analog voltage signal for a predetermined time in the sample-and-hold circuit. The A/D converter converts the analog voltage signal as held in the sample-and-hold circuit to a digital voltage signal and outputs the same to a frame memory which is capable of recording the digital voltage signal in a unit corresponding to a frame of x-ray image. The signal processing circuit is further provided with amplifiers for amplifying the analog voltage signals, and a multiplexer which sequentially selects the sample-and-hold circuits of the CDS circuits of the respective pixel columns to feed the analog voltage signal selectively from one sample-and-hold circuit to the A/D converter.

U.S. Pat. No. 7,122,802 (corresponding to Japanese Patent Laid-Open Publication No. 2004-000564) describes a signal processing circuit which is provided with integration amplifiers (reading portion circuits), an A/D converter (converting portion circuit), and first and second buffer memories (line buffers) located in between the A/D converter and a memory (collecting subsystem). The first and second buffer memories are line memories, each of which is capable of recording the digital voltage signal from a line of pixels of the pixel array, which corresponds to a line of x-ray image. An image reading operation for reading a frame of x-ray image is executed by the signal processing circuit in the manner as shown in FIG. 16. The signal processing circuit executes so-called pipeline processing, wherein an image signal P(N), which is an analog voltage signal obtained by converting signal charges p(N) of a line of pixels through integration amplifiers in one image reading cycle ($N^{th}$ cycle), is sampled and held in CDS circuits immediately before the next or $(N+1)^{th}$ cycle; the sampled and held image signal P(N) is converted to a digital image signal Pd(N) through the A/D converter and the digital image signal Pd(N) is temporarily stored in the first buffer memory in the $(N+1)^{th}$ cycle (see "AD Data" of FIG. 16); and the image signal Pd(N) is output from the first buffer memory (see "Data Out" of FIG. 16) in the cycle after the next, the $(N+2)^{th}$ cycle. Accordingly, in one cycle, a signal inputting operation, i.e. analog-to-digital conversion of an image signal through the A/D converter and temporary storage of the image signal in one buffer memory, is carried out in parallel or concurrently with a signal outputting operation, i.e. reading a digital image signal Pd(N−1) from the other buffer memory, the signal Pd(N−1) having been temporarily stored in the preceding cycle.

The buffer memory cannot store the voltage signal for one line unless the previously stored voltage signal for one line is output from the same buffer memory. Accordingly, if there is merely one buffer memory in the signal processing circuit, it is impossible to make the pipeline processing or parallel input and output of the voltage signals. Therefore, one cycle from the start of reading the analog voltage signal for one line till the end of writing the corresponding digital voltage signal in the memory inevitably involves the time for inputting the voltage signal in the buffer memory plus the time for outputting the same signal from the buffer memory.

In contrast to this, the pipeline-type signal processing circuit described in the prior art, as having the dual buffer memories, can make outputting operation of the voltage signal, which has been written in one buffer memory in the preceding cycle, simultaneously with inputting operation of the voltage signal, which has been sampled and held in the CDS circuits in the current cycle, into the other buffer memory. In other words, the signal inputting operation for one line and the signal outputting operation for the preceding line are simultaneously executed in one cycle. Therefore, the pipeline processing will cut the time taken for reading out a frame of image nearly in half as compared to the case using a single buffer memory. However, because the voltage signal for one line is read out from the buffer memory in the cycle next to the cycle in which the same voltage signal was written in the same buffer memory, the time lag from the sampling of analog image signal "P", obtained by integrating the signal charges "p" for one line, till the output of corresponding digital voltage signal "Pd" from the signal processing circuit gets approximately equal to one cycle period "T".

In FIG. 16, "Sync" represents a synchronizing signal which determines the period T of one cycle in which the signal processing circuit executes sampling and holding of the analog image signal P, digital conversion to the digital image signal Pd, temporary storage of the digital image signal Pd, and outputting of the digital image signal; "Internal Reset" represents a signal for executing at least one of those resetting operations for resetting charges in the integration amplifiers, resetting the sampling and holding in the CDS circuits, and selective resetting of the CDS circuits from selected condition to unselected condition; and "Analog Clock" represents a signal for timing the control of operations of the integration amplifiers and the CDS circuits, which constitute an analog signal processing circuit (analog front end). Specifically, the Analog Clock signal determines the timing of charge integration in the integration amplifiers, the timing of outputting the voltage signals to the CDS circuit, the timing of sampling and holding, and etc. "ADC Clock" and "Buffer Data Clock" represent control signals for the A/D converter and the buffer memories, respectively.

The chart "Active Buffer" indicates which buffer memory is used for writing the image signal Pd in the current cycle. Namely, the first and second buffer memories alternately serve as the active buffer, switched over with each cycle. For example, the image signal Pd(N) of one line is temporarily stored in the first buffer memory, and the image signal Pd(N+1) of the next line in the second buffer memory.

In the FPD type image detector, because the pixels accumulate unnecessary charges that result from dark currents or residual charges from the previous imaging may remain in the pixels, the FPD periodically carries out charge-resetting operation for clearing unnecessary charges off the pixels before starting charge accumulating operation, in order to reduce the influence of dark charge noises on x-ray images to the minimum. Accordingly, it is generally necessary for the radiography system using the FPD to synchronize the timing of x-ray radiation with the end of charge-resetting operation and the start of charge accumulating operation. For this purpose, in one radiography system, the source controller unit and the x-ray image detector are provided with interfaces (I/F) to establish mutual communication therebetween. The source controller unit sends a synchronizing signal to the electronic cassette at the time of starting x-ray radiation, so that the synchronizing signal triggers the x-ray image detector to proceed to the accumulating operation.

In another radiography system, the x-ray image detector and the source controller are not connected nor exchange any synchronizing signal with each other. Instead, a dose sensor is provided to measure the amount of radiated x-rays. The measured x-ray amount is compared with a predetermined threshold level so as to determine the start of radiation from the x-ray source when the x-ray amount goes over the threshold level. Upon the start of radiation being detected, the x-ray image detector drives the FPD to start charge accumulating operation. Likewise, the amount of x-rays measured by the dose sensor may be compared with another threshold level for determining the end of radiation from the x-ray source and driving the FPD to proceed from charge accumulating operation to reading operation.

Some radiography systems make an automatic exposure control (AEC), whereby the amount of x-rays dosed onto the subject is measured by a dose sensor during the imaging (exposure to x-rays) in order to stop x-ray radiation from the x-ray source when the integrated amount of x-rays measured by the dose sensor gets to a predetermined threshold level. Simultaneously, the x-ray image detector is controlled to proceed from charge accumulating operation to reading operation. The amount of x-rays radiated from the x-ray source is determined as a product of tube current and radiation time (mAs), because the tube current determines the amount per unit time of x-rays from the x-ray source. Although there are recommendable values for image acquisition settings, including the radiation time and the tube current, predetermined according to the target site of the subject, such as chest or head, the sex and age of the subject and the like, x-ray permeability also varies from individual to individual, e.g. depending upon the body constitution of the subject. Therefore, the AEC processing is conducted for acquiring more adequate image quality.

Conventionally, an ion chamber or the like has been used as a dose sensor. However, many techniques of modifying pixels of the FPD so as to serve the modified pixels as detective pixels for detecting the amount of radiation or dose have recent been suggested. For example, U.S. Patent Application Publication No. 2011/0180717 (corresponding to Japanese Patent Laid-Open Publication No. 2011-174908) describes connecting some pixels to a detective line for detecting radiation, not to the signal lines, directly without any switching element therebetween, such that charges generated in these pixels flow through the detective line regardless of ON-OFF operation of switching elements of ordinary pixels. The detective line is connected to a signal processing circuit, so that the signal processing circuit samples a voltage signal corresponding to the charges generated from the detective pixels, hereinafter referred to as the dose detection signal, at predetermined intervals. The sampled voltage signal is input to a controller, so that the controller makes an AEC (automatic exposure control) or detects a start or an end of x-ray radiation from the x-ray source on the basis of the dose detection signal.

According to the discloser in U.S. Patent Application Publication No. 2011/0180717 (corresponding to Japanese Patent Laid-Open Publication No. 2011-174908), the detective pixels are connected to the specific detective line for dose detection, and the detective line is connected to the specific signal processing circuit used especially for dose detecting operation. As an alternative, it has also been suggested that ordinary signal lines for ordinary pixels and a signal processing circuit for image signals may also serve to acquire the dose detection signal from the detective pixels. More than one detective pixel may be connected to one signal line. In the dose detecting operation, signal charges from the detective pixels are read out all at once through respective signal lines at each sampling operation.

In a radiography system in which the dose detection signal is acquired through signal lines for ordinary pixels and a signal processing circuit for image signals, if the signal processing circuit is configured to make the above-described pipeline processing, a problem could occur in relation to the AEC processing. That is, there would be a certain delay in deciding the time to stop the x-ray radiation or in detecting the start or the end of x-ray radiation. As a result, the subject could be overexposed, or the delay in operation of the FPD could result an artifact in the consequent x-ray image, degrading the image quality. The reason for such problem is because the pipeline-type signal processing circuit involves the time lag of approximately one cycle period from the integration of the signal charges till the output of the corresponding digital voltage signal (or the dose detection signal). If, for example, the x-ray radiation starts actually at the same time as the integration amplifiers start integration, the start of radiation will be determined on the basis of the dose detection signal with such a delay time that is almost triple the cycle period.

Specifically, when the pipeline-type signal processing circuit is used for the dose detecting operation, if the processing circuit would operate in constant cycles in the same manner as for the image reading operation as shown in FIG. 16, timing charts of the dose detecting operation would be as shown in FIG. 17. The timing charts of FIG. 17 are substantially equal to those of FIG. 16, but the image signals (signal charges "p" of the pixels, the analog image signal "P" and the digital image signal "Pd") are replaced with dose detection signals (signal charges "s" of the detective pixels, an analog dose detection signal "S" and a digital dose detection signal "Sd"), and one cycle period is designated by Ts.

In the image reading operation, the image signal is read line-sequentially, i.e., one line in each cycle T, so that the time taken for reading out a frame of image (all pixels) approximately equals T multiplied by the total number of lines. On the other hand, the dose detecting operation is configured to read the charges from the detective pixels at once through the respective signal lines, so that the charges of all detective pixels are sampled as a dose detection signal in each cycle Ts. For detecting the start of radiation, a dose detection signal obtained through the current or $N^{th}$ time of sampling is compared with a dose detection signal obtained through the preceding or $(N-1)^{th}$ time of sampling, to determine whether the signal level increases or not.

As described above, the conventional pipeline-type signal processing circuit involves the time lag of approximately one cycle period Ts from the integration of the signal charges till the output of the corresponding digital voltage signal. Therefore, if, for example, the x-ray radiation starts actually at the start of the $N^{th}$ sampling (integration of charges s(N) of the detective pixels through the integrating amplifiers), as shown in FIG. 17, the digital dose detection signal Sd(N) obtained through the $N^{th}$ sampling will be output from the buffer memory with a delay time of almost triple the cycle period (3Ts). This results in a corresponding delay in determining the start of radiation.

Beside the above problem, since the response of the x-ray source is low and hence the dose amount shows a small change per unit time in the initial stage of radiation, the cycle period Ts (50 to 500 µsec.) for sampling the dose detection signal is preferably set longer than the cycle period T for reading the image signal P, in order to ensure a sufficient S/N ratio. With the elongated cycle period Ts, the delay of almost triple the cycle period, due to the pipeline processing, cannot be ignored as a margin of error in the dose detecting operation. Particularly, when each radiation time is set as short as several micro seconds for the sake of total dose reduction, i.e. minimum exposure to x-rays, the delay of detection causes an unignorable problem.

The above prior arts do not disclose any solution for the above problem in obtaining the dose detection signal from the dose sensor through the pipeline-type signal processing circuit.

SUMMARY OF THE INVENTION

In view of the foregoing, an object of the present invention is to provide a radiographic image detector and a controlling method therefor, which enable processing based on a signal output from a dose sensor as shortly after the dose sensor outputs the signal as possible, even while the signal from the dose sensor is obtained through a pipeline-type signal processing circuit.

According to the present invention, a radiographic image detector for detecting radiographic images of a subject comprises a flat panel detector (FPD), a pipeline-type signal processing circuit, a memory and a controller for controlling operation timings of the FPD, the signal processing circuit and the memory.

The FPD has an imaging area in which a plurality of columns of pixels for accumulating electric charges corresponding to the amounts of radioactive rays incident on the pixels, a dose sensor generating electric charges corresponding to the amount of radiated radioactive rays radiated from a radiation source, and signal lines provided for respective columns of the pixels are arranged in an array, wherein the pixels and the dose sensor are connected to the signal lines to output the electric charges accumulated in the pixels as image signals and the electric charges generated from the dose sensor as a dose detection signal through the signal lines. The pipeline-type signal processing circuit comprises a plurality of integrating amplifiers provided for the respective signal lines, to integrate and convert electric charges to voltage signals, and first and second signal holding devices for temporarily holding two sets of voltage signal as successively read out from the integrating amplifiers, wherein a set of voltage signal is being input to one of the first and second signal holding devices while a preceding set of voltage signal is being output from the other of the first and second signal holding devices. The memory stores the image signal and the dose detection signal as voltage signals output from the signal processing circuit.

In a reading operation for outputting the image signal to the memory, the controller controls the signal input and output of the first and second signal holding devices to be repeated in ordinary cycles of a constant length which corresponds to an integrating session from a start of integration of electric charges till resetting the integrating amplifiers.

In a dose detecting operation for outputting the dose detection signal to the memory, the controller controls the signal input and output of the first and second signal holding devices to be repeated in two kinds of cycles, including primary cycles and secondary cycles of a shorter length than the primary cycles, in such a manner that at least one secondary cycle is conducted in between two primary cycles.

The dose detection signal may be used for at least one of determination of whether the radiation source has started radiation, determination of whether the radiation source has stopped radiation, automatic control of radiographic exposure, and gain control on the image signal in the reading operation.

In each ordinary cycle, each of the integrating amplifiers integrates electric charges of one pixel per one signal line to output the image signal for one line.

The dose sensor preferably comprises a plurality of elements dispersed over the imaging area, and the integrating amplifiers integrate electric charges from the plurality of elements of the dose sensor all at once in the primary cycle and in the secondary cycle.

The primary cycle is preferably longer than the ordinary cycle.

In the dose detecting operation, among of the two sets of voltage signal as being successively readout from the integrating amplifiers, only one set of voltage signal which is input in the first signal holding device or the second signal holding device is treated as the dose detection signal, and the other set of voltage signal is not treated as the dose detection signal but as a dummy signal containing useless data.

One integrating session of the integrating amplifiers, which is set for the dose detecting operation, may be divided between the primary cycle and the secondary cycle.

Alternatively, one integrating session of a corresponding length may be allotted to each of the primary and secondary cycles.

The signal processing circuit further comprises CDS circuits connected to respective outputs of the integrating amplifiers, to sample and hold an analog voltage signal from the integrating amplifiers, and an A/D converter for converting the analog voltage signal sampled and held in the CDS circuits to a digital voltage signal.

In one embodiment, the first and second signal holding devices are two buffer memories connected in parallel with each other in between the A/D converter and the memory. In another embodiment, the CDS circuits are connected in pairs to the respective outputs of the integrating amplifiers, and the CDS circuits of each pair are connected in parallel with each other to constitute the first and second signal holding devices respectively. The controller preferably conducts the primary cycles and the secondary cycles alternately.

In still another embodiment, one and the other of a pair of buffer memories, which are connected in parallel with each other in between the A/D converter and the memory, and one and the other of a pair of the CDS circuits, which are connected in parallel with each other to the output of each integrating amplifier, constitute the first signal holding devices and the second signal holding devices, respectively. The controller conducts two secondary cycles in between two primary cycles.

The controller cuts the length of the secondary cycle shorter than the primary cycle by controlling the numbers or intervals of operation control signals applied to the signal processing circuit.

The dose sensor may be constituted of some of the pixels. Specifically, the pixels include ordinary pixels that accumulate signal charges responding to radioactive rays and output the signal charges to the signal lines upon switching elements being turned on, and detective pixels that serve as the dose sensor. The detective pixels may preferably be connected directly to the signal lines without intermediate switching elements. Alternatively, the detective pixels may be provided with such switching elements that are driven independently of the switching elements of the ordinary pixels, the detective pixels serving as the dose sensor.

The radiographic image detector is preferably an electronic cassette containing the FPD in a portable housing.

A method of operating the radiographic image detector in accordance with the present invention comprises the steps of: making the controller, in a reading operation for outputting the image signal to the memory, control the signal input and output of the first and second signal holding devices to be repeated in ordinary cycles of a constant length corresponding to an integrating session from the start of integration of electric charges to resetting the integrating amplifiers; and making the controller, in a dose detecting operation for outputting the dose detection signal to the memory, control the signal input and output of the first and second signal holding devices to be repeated in two kinds of cycles, including primary cycles and secondary cycles of a shorter length than the primary cycles, in such a manner that at least one secondary cycle is conducted in between the $(N-1)^{th}$ primary cycle and the $N^{th}$ primary cycle.

As the pipeline-type signal processing circuit carries out the dose detecting operation by repeating the primary cycles and the shorter secondary cycles in such a manner that at least one secondary cycle is conducted in between two primary cycles, the dose detection signals will be output at shorter intervals than in the case where the dose detecting operation is carried out in constant cycles.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 17 shows timing charts of a dose detecting operation conducted by the pipeline-type signal processing circuit in constant cycles like in the image reading operation.

DESCRIPTION OF THE PREFERRED EMBODIMENTS

[First Embodiment]

Figure 1:
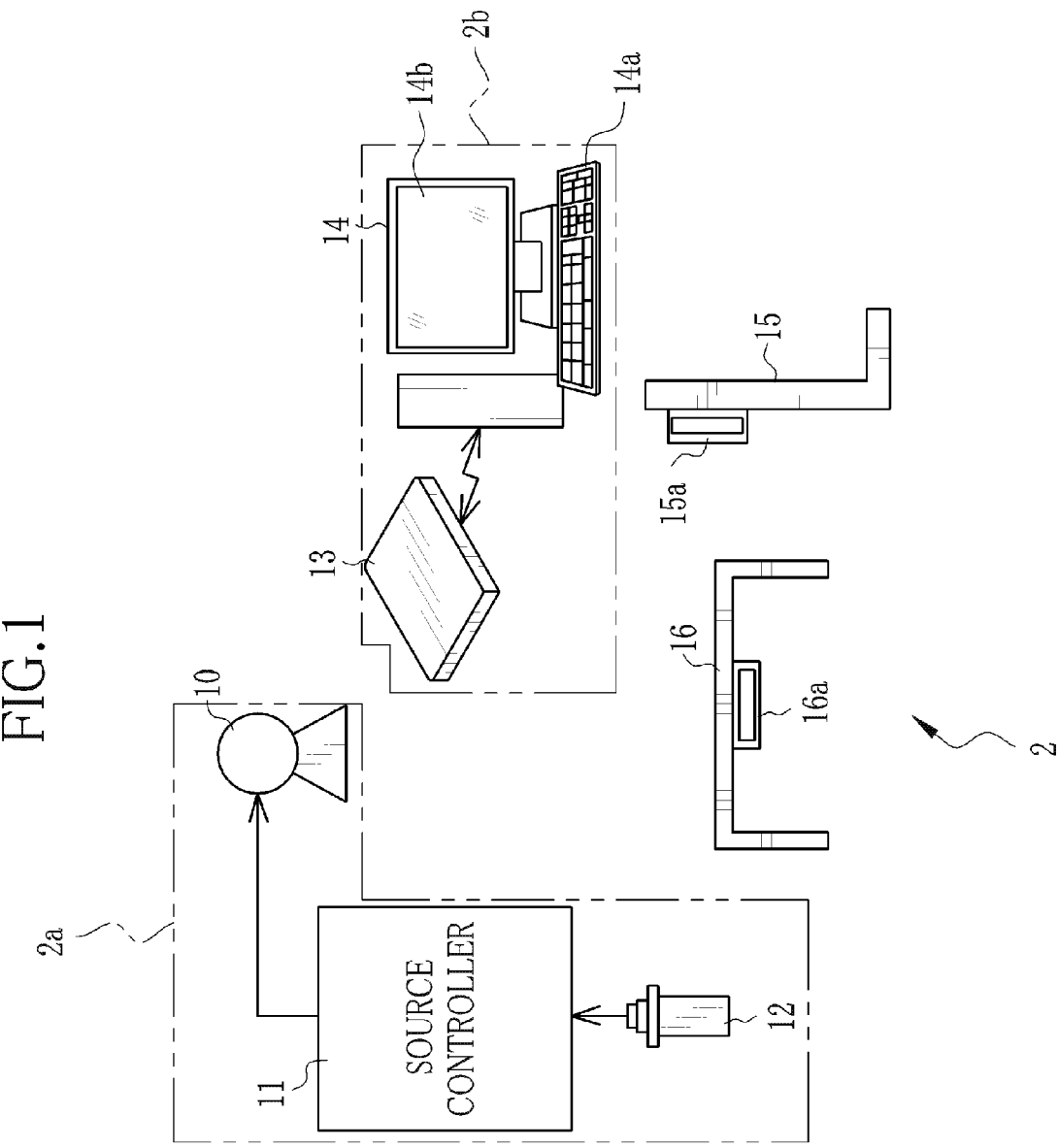
FIG. 1 is a diagram schematically illustrating an x-ray radiography system.

In FIG. 1, a radiography system 2 includes an x-ray source 10, a source controller unit 11 for controlling the x-ray source 10, an activator switch 12 for instructing a start of radiation from the x-ray source 10, an electronic cassette 13 as a radiographic image detector, a console 14 for controlling operation of the electronic cassette 13 and processing x-ray images acquired through the electronic cassette 13, a radiographic stand 15 for imaging a subject in the standing posture and a radiographic table 16 for imaging a subject lying thereon. The x-ray source 10, the source controller unit 11 and the activator switch 12 constitute an x-ray projector 2a, whereas the electronic cassette 13 and the console 14 constitute an x-ray imaging apparatus 2b. The x-ray projector 2a and the x-ray imaging apparatus 2b are not equipped with any mutual communication device, whereas the electronic cassette 13 has a function to determine the start of radiation from the x-ray projector 2a. The radiography system 2 further includes a source positioning mechanism for setting the x-ray source 10 to a designated position in a designated direction and other equipment, although they are not shown in the drawings. The x-ray source 10 is shared by the radiographic stand 15 and the radiographic table 16.

The x-ray source 10 has an x-ray tube for radiating x-rays and a collimator for limiting the irradiation field of x-rays from the x-ray tube. The x-ray tube has a cathode which includes a filament for emitting thermions and an anode (target) against which the thermions strike to radiate x-rays. The collimator may for example be made of lead plates, which shield x-rays and are assembled into a double-cross formation having a center aperture for letting x-rays pass through it. The lead plates are movable so as to change the size of the center aperture to confine the irradiation field to a suitable range.

The source controller unit 11 includes a high voltage generator which boosts up an input voltage through a transformer to generate a high level tube voltage and supplies the tube voltage to the x-ray source 10 through a high voltage cable, and a controller for controlling tube voltage, tube current and x-ray radiation time. The tube voltage determines energy spectra of x-rays from the x-ray source 10, and the tube current determines the amount of radiation per unit time. The tube voltage, tube current, radiation time and other image acquisition settings are manually designated by an operator, such as a radiologist, through an operation panel of the source controller unit 11.

The activator switch 12, which is operated by a radiologist, may be a two-step pushbutton switch that outputs a warm-up start signal for staring warming up the x-ray source 10 upon being pushed to the first step (to the half). Thereafter, upon being pushed further to the second step (to the full), the activator switch 12 outputs a radiation starting signal for letting the x-ray source 10 start radiation. These signals are fed through a signal cable to the source controller unit 11.

The controller of the source controller unit 11 starts supplying power from the high voltage generator to the x-ray source 10 upon receipt of the radiation starting signal from the activator switch 12. When the set radiation time has elapsed, the controller stops the power supply from the high voltage generator to the x-ray source 10. The radiation time is variable according to the image acquisition settings, but the maximum radiation time for acquiring a still image is mostly determined within a range of about 500 milliseconds to 2 seconds. The upper limit of the radiation time is decided by the maximum radiation time.

The console 14 is communicably connected to the electronic cassette 13 through wired or wireless communication, to control the operation of the electronic cassette 13 according to input operations by the operator on an input device 14a such as a keyboard. An x-ray image sent from the electronic cassette 13 is displayed on a monitor 14b of the console 14, and also stored in a storage device, such as a HDD or a memory inside the console 14, or an external storage device like an image database server to which the console 14 is connected through a network.

The console 14 may receive examination orders, including information on the sex and age of the subject, the purpose of imaging, etc., and display the received examination orders on the monitor 14b. The examination orders may be issued by external systems, such as a hospital information system (HIS) and a radiological information system (RIS), which manage information on patients and information on radiological examinations. The examination orders may also be manually input by an operator or radiologist. The examination order also includes the target site to be imaged, e.g. head, chest or abdomen, and the imaging direction, such as frontal, lateral, diagonal, posterior-to-anterior (PA) or anterior-to-posterior (AP) irradiation. The operator checks the content of each examination order on the monitor 14b, and input the image acquisition settings according to the examination order through operation screens on the monitor 14b.

Through the console 14, various parameters, including the tube voltage, tube current and radiation time, may be input as image acquisition settings in the same way as in the source controller 11. The console 14 stores these parameters for respective sites to be imaged, so that the operator can set proper imaging conditions for each target site by designating the target site. Since the cumulative amount of radiation is determined as a product of tube current and radiation time, it may be possible to designate a value of the product of tube current and radiation time, i.e. mAs value, as one imaging condition in the source controller 11 or the console 14. The image acquisition settings may be manually input in the source controller 11 by the operator with reference to the same settings in the console 14.

Figure 2:
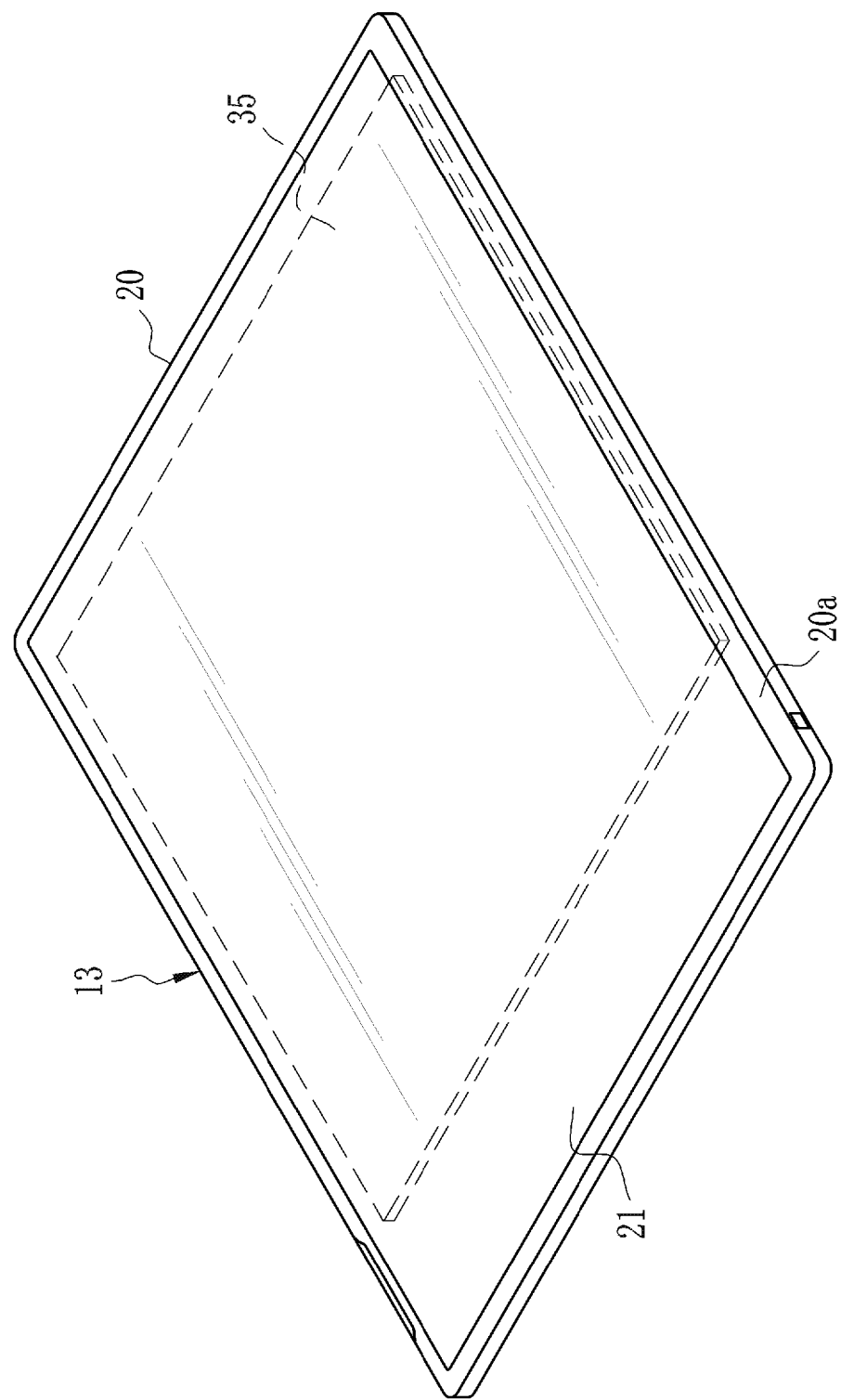
FIG. 2 is a perspective view illustrating an appearance of an electric cassette.

Referring to FIG. 2, the electronic cassette 13 mainly consists of a flat panel detector (FPD) 35 and a flat planer portable housing containing the FPD 35. The housing 20 is made for example of conductive resins. A rectangular opening is formed through a front surface 20a of the housing 20, and a transparent top panel 21 is fitted in the opening. X-rays are incident through this opening. The transparent panel 21 is made of a carbon material that is light, highly rigid and highly permeable to x-rays. The housing 20 doubles as a shield against electromagnetic waves, shielding the interior of the electronic cassette 13 from electromagnetic noises and preventing leakage of electromagnetic waves from the electronic cassette 13.

The housing 20 of the electronic cassette 13 has a plane size approximately equal to that of radiographic film cassettes and IP cassettes (imaging plate cassettes) which may also be called computed radiography cassettes (CR cassette), dimensioned according to ISO 4090:2001 standard. Generally, more than one electronic cassette 13 is disposed for one radiography system 2. For example, two electronic cassettes 13 are disposed respectively for the radiographic stand 15 and the radiographic table 16 in each x-ray room. The electronic cassette 13 can be detachably attached to the radiographic stand 15 or table 16. Besides being used in the radiographic stand 15 or the radiographic table 16, the electronic cassette 13 may be used independently. For example, the electronic cassette 13 may be put directly on a bed on which the subject is lying, or may be held by the subject. Because being sized to be approximately equal to the film cassettes and the IP cassettes, the electronic cassette 13 can be mounted to a conventional radiographic stand or table which is adapted to the film cassettes and IP cassettes.

Figure 3:
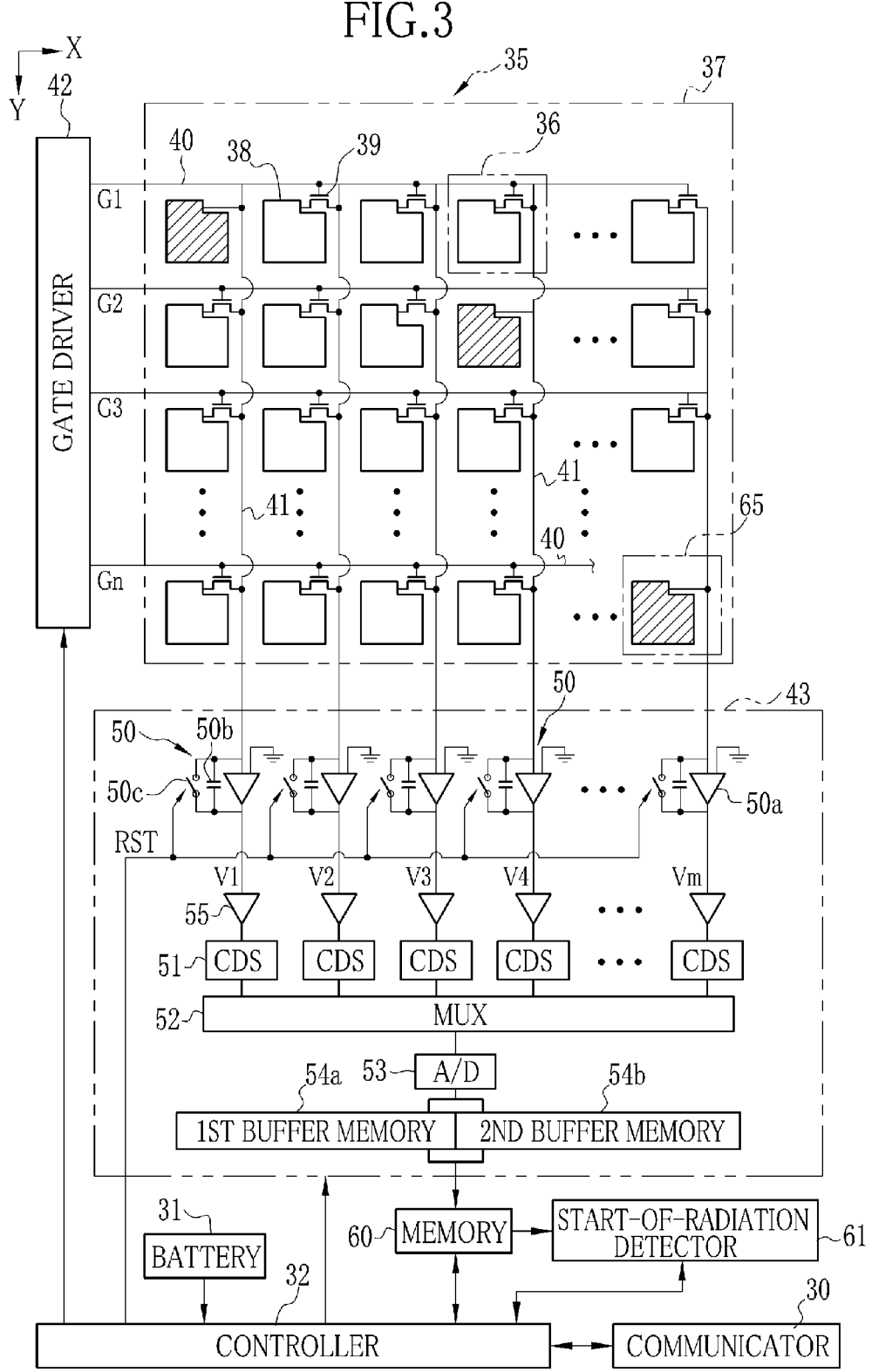
FIG. 3 is a block diagram illustrating an internal structure of an electronic cassette.

Referring to FIG. 3, a communicator 30 for wired or wireless communication with the console 14 and a battery 31 are incorporated in the electronic cassette 13. The communicator 30 intermediates data transmission between the console 14 and a controller 32, the data including image data and control signals. The battery 31 supplies power for actuating components of the electronic cassette 13. The battery 31 should be of a smaller size for the sake of compactness of the thin electronic cassette 13. The battery 31 may be rechargeable using an external specific charging device, called cradle. The battery 31 may also be configured to be wirelessly rechargeable.

The communicator 30 may be connected to the console 14 through a cable when the wireless communication between the electronic cassette 13 and the console 14 is not available, for example, because of the run-out of the battery 31. When the cable from the console 14 is connected to the communicator 30, the electronic cassette 13 can communicate with the console 14 through the cable, and may also be power-supplied from the console 14.

The FPD 35 has a thin film transistor (TFT) active matrix substrate with an imaging area 37 formed thereon. The imaging area 37 is constituted of an array of pixels 36 for accumulating signal charges according to the incident amount of x-rays. The pixels 36 are arranged in a matrix (n-lines and m-columns) at predetermined intervals; the line direction and the column direction of the pixel matrix correspond to x-direction and y-direction of the imaging area 37, respectively. Note that "n" and "m" represent plural integers, e.g., m, n=around 2000. The arrangement of the pixels 36 is not limited to a square matrix array, but may be a honeycomb array.

The FPD 35 is of an indirect conversion type that has a not-shown scintillator (a phosphorous member) for converting x-rays to visible rays and converts the visible rays to electric charges through the pixels 36. The scintillator is positioned to face to the whole imaging area 37. The scintillator is made of a phosphor such as cesium iodide (CsI) or gadolinium oxy sulfide (GOS). Note that the scintillator and the FPD 35 may be arranged in the PSS (penetration side sampling) style, wherein the scintillator and the FPD 35 are arranged in this order from the direction in which the x-rays are incident, or may be arranged in the ISS (irradiation side sampling) style, wherein the FPD 35 and the scintillator are arranged in the opposite order. The FPD 35 may also be of a direct conversion type using a conversion layer that converts x-rays directly to electric charges; the conversion layer may for example be made of amorphous selenium.

Each pixel 36 includes a photoelectric converter section 38 and a thin film transistor (TFT) 39 as a switching element. The photoelectric converter section 38 generates electric charges (electrons-positive holes) in response to incident visible rays and accumulates the generated electric charges.

The photoelectric convertor section 38 is constituted of a semiconductor layer, e.g. PIN-type layer, and upper and lower electrodes provided on the top and bottom of the semiconductor layer. The photoelectric converter section 38 is connected at its lower electrode to the TFT 39 and at its upper electrode to a not-shown bias line. The bias lines are provided in same number as the number "n" of rows of pixels 36 of the imaging area 37. Hereinafter, each row of pixels 36 will be referred to as a pixel line, because a line of x-ray image is acquired on the basis of signal charges from a row of pixels 36. The bias lines are connected together to a bus line, which is connected to a bias power source. Through the bus line and the respective bias lines, a bias voltage is applied to the upper electrodes of the photoelectric converter sections 38. The applied bias voltage induces an electric field in the semiconductor layer of each photoelectric converter section 38. Because of the induced electric field, the electric charges (pairs of electrons and holes) generated through the photoelectric conversion in the semiconductor layer will move to the opposite electrodes; the electrons move to the upper electrode of positive polarity, whereas the holes move to the lower electrode of negative polarity. As a result, electric charges are accumulated in the photoelectric convertor section 38.

The TFT 39 is connected at its gate to a scanning line 40, at its source to a signal line 41, and at its drain to the photoelectric converter section 38. The scanning lines 40 and the signal lines 41 are arranged in a grid. The scanning lines 40 are provided for the respective rows of pixels 36 ("n" pixel lines), each scanning line being connected to a row of pixels 36. The signal lines 41 are provided for the respective columns of pixels 36 ("m" pixel columns) such that each signal line 41 is connected to a column of pixels 36. The scanning lines 40 are connected to the gate driver 42, whereas the signal lines 41 are connected to the signal processing circuit 43.

The gate driver 42 drives the TFTs 39 to make accumulating operation for accumulating the signal charges in the pixels 36, reading operation for reading out the signal charges from the pixels 36, or charge-resetting operation for resetting the signal charges accumulated in the pixels 36. The controller 32 controls the timings to start the respective operations executed by the gate driver 42.

The accumulating operation is carried out by turning off the TFTs 39. While the TFT 39 is off, signal charges are accumulated in the pixel 36. In the reading operation, the gate driver 42 sequentially outputs gate pulses G1 to Gn, one gate pulse to one scanning line 40, thereby to activate the scanning lines 40 one after another. Thus, the TFTs 39 of the activated scanning line 40 are turned on line by line. When the TFTs 39 of one line are turned on, the signal charges accumulated in the pixels 36 of this line are fed through the respective signal lines 41 to the signal processing circuit 43. For reduced total reading time, it may be possible to make thinning reading, wherein the gate pulses are generated to every few lines to read the charges merely from these lines, or binning reading, wherein the gate pulses are given to multiple lines at a time to read the charges concurrently from these lines.

As well known in the art, dark charges will be generated in the semiconductor layer of the photoelectric converter sections 38 regardless of whether x-rays are incident or not. The dark charges will be accumulated in the photoelectric converter section 38 of each pixel 36 as the bias voltage is applied thereto. Since the dark charges turn to be a noise component to image data, the charge-resetting operation is executed at predetermined intervals to sweep off the dark charges from the pixels 36 through the signal lines 41.

The resetting operation may be executed for example according to a line-sequential method, whereby the pixels 39 are to be reset line by line. According to the line-sequential resetting method, the gate driver 42 sequentially outputs the gate pulses G1 to Gn to the respective scanning lines 40, like in the reading operation, to turn on the TFTs 39 line by line.

The charge-resetting operation may also be carried out according to a parallel resetting method or an allover resetting method. According to the parallel resetting method, pixel lines are subdivided into groups, and the dark charges are cleared off the pixels line by line within the respective groups in parallel to other groups. According to the allover resetting method, the gate pulses are simultaneously applied to all lines to sweep the dark charges off all pixels at once. These methods may speed the charge resetting operation.

Figure 4:
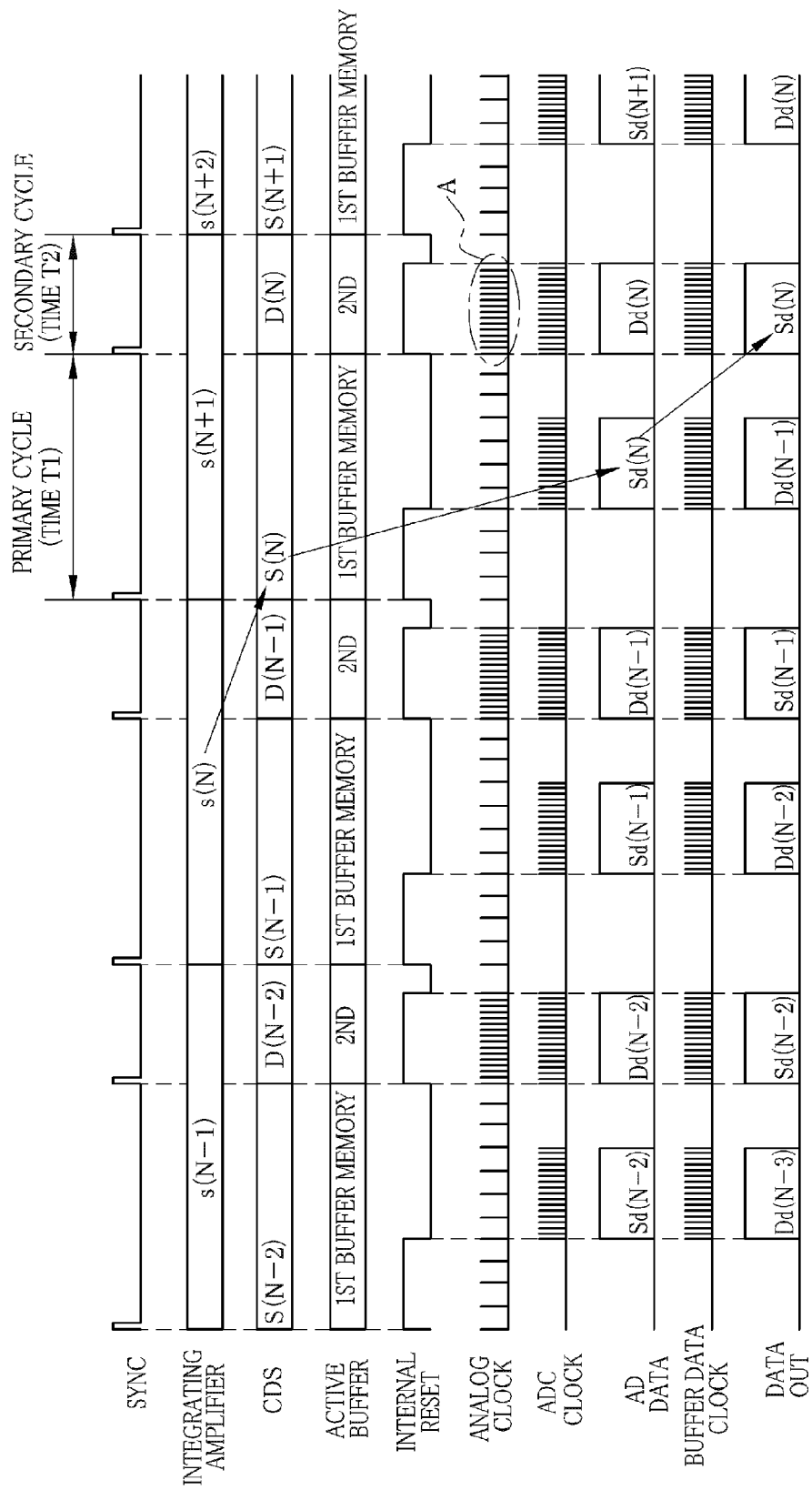
FIG. 4 shows timing charts of a dose detecting operation conducted by a pipeline-type signal processing circuit.
Figure 16:
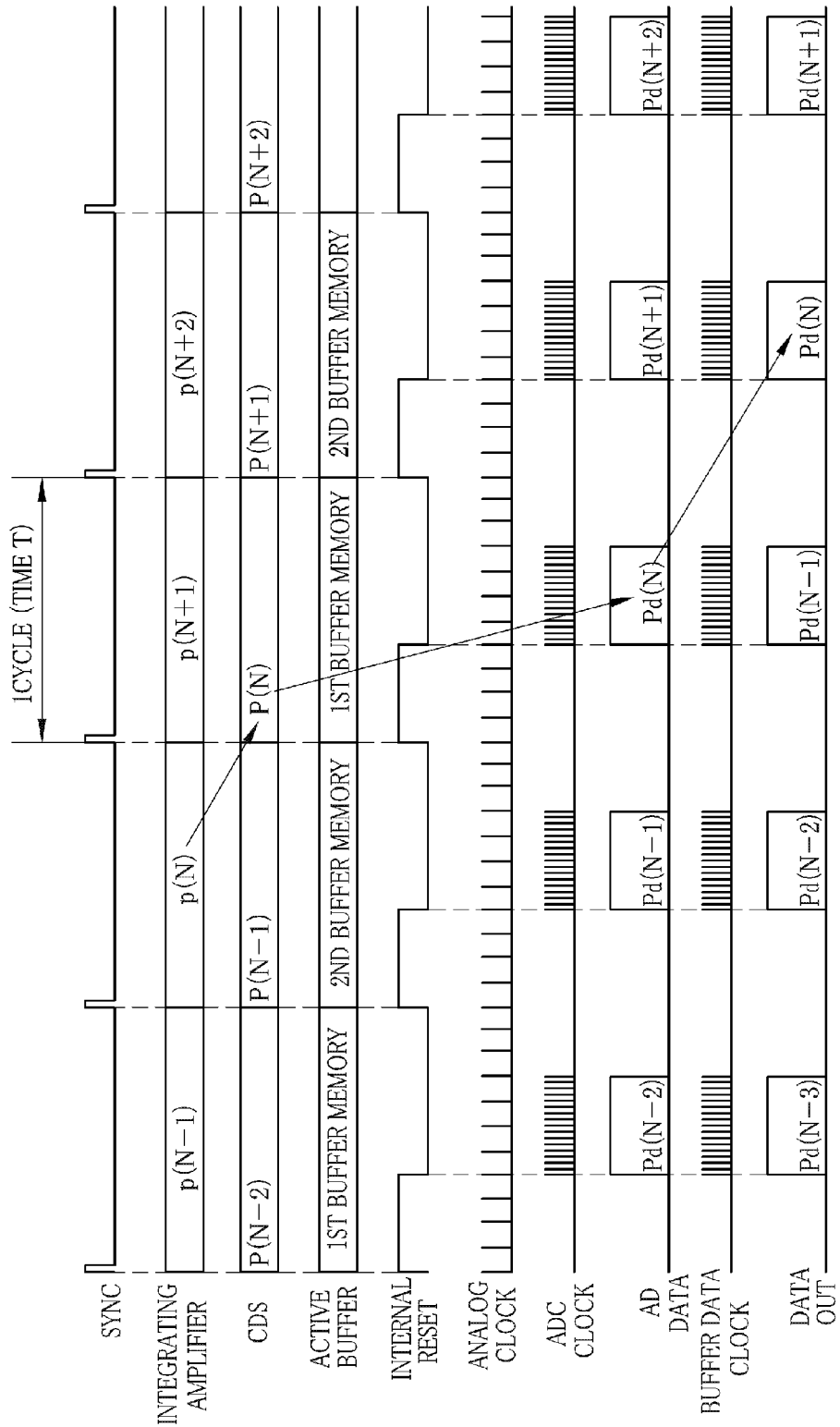
FIG. 16 shows timing charts of an image reading operation of a pipeline-type signal processing circuit.

The signal processing circuit 43 is an application specific integrated circuit (ASIC) that executes pipeline processing on the basis of various operation control signals, including a synchronizing signal "Sync", an internal reset signal "Internal Reset" and an analog clock signal "Analog Clock" (see FIG. 4). The signal processing circuit 43 cyclically makes the pipeline processing in constant cycles for reading the image signals, in the same way as the prior art shown in FIG. 16. On the other hand, in a dose detecting operation for detecting a dose detection signal Sd, which is used for example for determining the start of radiation, the signal processing circuit 43 makes the pipeline processing in primary cycles and secondary cycles of a shorter length than the primary cycle in such a manner that the secondary cycles are conducted in between the primary cycles, in order to speed the output of the dose detection signal Sd, as will be described in more detail later.

The signal processing circuit 43 includes integrating amplifiers 50, correlated double sampling (CDS) circuits 51, a multiplexer (MUX) 52, an A/D converter 53, and first and second buffer memories 54a and 54b.

The integrating amplifiers 50 are connected to the signal lines 41 in one-to-one relationship. Each integrating amplifier 50 consists of an operational amplifier 50a and a capacitor 50b connected between an input and an output of the operational amplifier 50a. The signal line 41 is connected to the input of the operational amplifier. Another input of the operational amplifier 50a is grounded. A reset switch 50c is connected in parallel with the capacitor 50b. The integrating amplifiers 50 integrate the signal charges from the signal lines 41 to convert them to analog voltage signals V1 to Vm. Output terminals of the individual integrating amplifiers 50 are connected to the MUX 52, individually through an amplifier 55 and the CDS circuit 51. The A/D converter 53 is connected to an output of the MUX 52.

The CDS circuit 51 has a couple of sample-and-hold circuits, renders the output voltage signal from the integrating amplifiers 50 with the correlated double sampling to eliminate noises therefrom, and holds the output voltage signal in the sample-and-hold circuits for a predetermined time. The MUX 52 sequentially selects one of the parallel-connected CDS circuits 51, to feed the voltage signals V1 to Vm from the integrating amplifiers 50 serially to the A/D converter 53. The A/D converter 53 converts the analog voltage signals V1 to Vm to a digital voltage signal, and output the same alternately to the first buffer memory 54a or the second buffer memory 54b, which are connected in parallel with each other.

The first and second buffer memories 54a and 54b constitute a signal holding section necessary for conducting the pipeline processing. Each buffer memory 54a or 54b is a line memory capable of storing the digital voltage signals representative of a line of x-ray image. The first and second buffer memories 54a and 54b have the same number "m" of memory cells as the number of pixel columns or signal lines, so that the digital voltage signals V1 to Vm of the individual pixel columns are stored in the respective memory cells. Each of the first and second buffer memories 54a and 54b temporarily stores the digital voltage signal for one line, which are output from the A/D converter 53, and then outputs the stored digital voltage signal to a memory 60, which is built in the electronic cassette 13. In the memory 60, the digital voltage signal for one line are recorded as image data representative of a line of x-ray image in association with respective locations of the corresponding pixels 36 in the imaging area 37, which are indicated as coordinate values. Thus, the reading operation for one line is accomplished. Note that an additional amplifier may also be connected in between the MUX 52 and the A/D converter 53.

When the voltage signals V1 to Vm for one line have been read out from the integrating amplifiers 50, the controller 32 outputs a reset pulse RST to the integrating amplifiers 50 to turn on the reset switches 50c. Thereby, the signal charges for one line, accumulated in the capacitors 50b, are discharged and reset to zero. After resetting the integrating amplifiers 50, the controller 32 turns off the reset switches 50c and, in a predetermined time thereafter, holds one of the sample-and-hold circuits of the CDS circuits 51 to sample kTC noise components from the integrating amplifiers 50. Thereafter, the gate driver 42 outputs the gate pulse to the next line, starting reading the signal charges from the pixels 36 of the next line. In a predetermined time after the output of the gate pulse, the signal charges of the next line pixels 36 are held in the other sample-and-hold circuits of the respective CDS circuits 51. These operations are sequentially repeated to readout the signal charges from all lines of pixels 36.

When the signal charges have been read out from all lines, image data of a frame of x-ray image is stored in the memory 60. The image data is read out from the memory 60 into the controller 32, to be processed for various image renderings. Thereafter, the processed image data is transmitted to the console 14 through the communicator section 30. Thus the x-ray image of the subject is detected.

In the charge resetting operation, as the TFTs 39 are turned on, the dark charges flow from the pixels 36 through the signal lines 41 into the capacitors 50b of the integrating amplifiers 50. However, unlike the reading operation, the MUX 52 does not read out the charges accumulated in the capacitors 50b in the resetting operation. Instead, the controller 32 outputs the reset pulses RST synchronously with the respective gate pulses G1 to Gn, to turn the reset switches 50c on, discharging the capacitors 50b to reset the integrating amplifiers 50.

The controller 32 is provided with not-shown image processing circuits for processing the x-ray image data from the memory 60 for various image renderings, such as offset correction, sensitivity correction and defect compensation. The offset correction circuit eliminates fixed-pattern noises, which are resulted from individuality of the signal processing circuit 43 or environmental condition during the imaging, from the x-ray image by subtracting an offset correcting image in pixel-to-pixel relationship from the x-ray image, the offset correcting image being obtained from the FPD 35 without being exposed to x-rays. The sensitivity correction circuit may be called a gain correction circuit, which corrects variations in sensitivity of the photoelectric convertor section 38 between the pixels 36, variations in output characteristics of the signal processing circuit 43 and the like. The defect correction circuit compensates for pixel levels of defective pixels through line-interpolation using pixel levels of normal pixels around the defective pixels on the basis of information about defective pixels, which is acquired through the inspection before shipment or periodical inspections for maintenance. The defect correction circuit also compensates for pixel levels of those pixels 36 which belong to the columns in which detective pixels 65 are positioned. The detective pixels will be described in detail below. Note that the above various image processing circuits may be provided in the console 14 so that the image data may be subjected to these image renderings in the console 14.

Besides the ordinary pixels 36, which are connected to the signal lines 41 through the TFTs 39 in the way as described above, the FPD 35 is provided with the detective pixels 65 in the same imaging area 37. The detective pixels are short-circuited or connected directly to the signal lines 41 without the TFT 39. The detective pixels 65 are used for measuring the amount of x-rays incident on the imaging area 37, serving as a dose sensor for use in determining the start of radiation from the x-ray source. In the drawings, the detective pixels 65 are hatched for discrimination from the ordinary pixels 36.

The detective pixels 65 are arranged in such a manner that the detective pixels 65 are distributed evenly over the whole imaging area 37. The detective pixels 65 are provided one in every third or fourth column of pixels 36, being connected to the same signal line 41 in each of these columns. The locations of the detective pixels 65 are known when the FPD 35 is manufactured, and are previously memorized as coordinate values in a not-shown non-volatile memory of the FPD 35. Alternatively, the detective pixels 65 may be located intensively in a portion of the imaging area 37; the arrangement of the detective pixels 65 may vary as appropriate. For example, in a mammography apparatus, the detective pixels 65 are preferably located intensively on the chest wall side. It is also possible to provide more than one detective pixel 65 in respective columns.

The pixels 36 and the detective pixels 65 have the same fundamental structure, including the photoelectric convertor section 38, except that the detective pixels 65 is directly connected to the signal line 41 without the TFT 39 being connected between the detective pixels 65 and the signal line 41. Therefore, the electric charges generated in the photoelectric convertor section 38 of the detective pixels 65 will always flow into the signal lines 41 regardless of whether the TFT 39s are on or off. That is, it is possible to read out the electric charges from the detective pixels 65 even during the accumulating operation while the TFTs 39 of the ordinary pixels 36 are off. Accordingly, the electric charges C (see FIG. 4) generated from the detective pixels 65 will always flow into the capacitors 50b of those integrating amplifiers 50 which are connected to the detective pixels 65 through the signal lines 41. The charges from the detective pixels 65 are accumulated in the integrating amplifiers 50 and then output as an analog voltage signal S to the A/D converter 53, through which the analog voltage signal S is converted to a digital voltage signal Sd, which will hereinafter be referred to as the dose detection signal Sd. The dose detection signal Sd is input to the first buffer memory 54a and, thereafter, output to the memory 60. To the second buffer memory 54b, a later-mentioned dummy signal Dd is input while the dose detection signal Sd is being output from the first buffer memory 54a, and the dummy signal Dd is output from the second buffer memory 54b while the next dose detection signal Sd is being input in the first buffer memory 54a. The FPD 35 repeats this dose detecting operation till a start-of-radiation detector 61 determines on the basis of the dose detection signals Dd that the x-ray radiation has been started.

The start-of-radiation detector 61 is driven under the control of the controller 32. The start-of-radiation detector 61 reads out the dose detection signal Sd from the memory 60 to determine the start of x-ray radiation on the basis of the read dose detection signal Sd. Specifically, the highest level of the dose detection signal Sd from the memory 60 is compared with a predetermined detection threshold for the start of x-ray radiation at every readout of the dose detection signal Sd. When the highest level of the dose detection signal Sd gets over the detection threshold, the start-of-radiation detector 61 determines that the x-ray source has started radiation, and outputs a radiation start detection signal to the controller 32. The detection threshold for detecting the start of x-ray radiation may be a constant level regardless of the image acquisition settings.

The signal processing circuit 43 operates in such a manner as shown in FIG. 4 during the dose detecting operation. In FIG. 4, the abbreviations or letter codes "Sync", "Analog Clock", "ADC Clock" and "Buffer Clock" represent the same or similar contents to those mentioned with respect to FIGS. 16 and 17, and the same applies to FIGS. 7 and 9. Therefore, detailed description of these will be omitted hereinafter. The "Internal Reset" signal is also used for resetting the integrating amplifiers 50, like in the examples of FIGS. 16 and 17. In the embodiment of FIG. 4, however, the integrating amplifiers 50 are not reset at the ends of the primary cycles, but only reset at the ends of the secondary cycles following the primary cycles. The letter code "$2^{nd}$" in FIG. 4 stands for the second buffer memory 54b, and the same applies to FIG. 9.

According to the embodiment as shown in FIG. 4, the signal processing circuit 43 conducts primary and secondary cycles in pairs in the dose detecting operation; the primary and secondary cycles alternate with each other. The secondary cycle is configured to be extremely shorter than the primary cycle, unlike the image reading operation wherein the length of every cycle is constant. In order to achieve a sufficient S/N ratio of the dose detection signal Sd, the length T1 of the primary cycle is set longer than the constant cycle period T for the image reading gets (T1>T). For example, the primary cycle period T1 is 50 to 500 μsec., which is several times to several-ten times of the length T of the ordinary cycle T for image reading. Moreover, the total length of the primary and secondary cycles T1+T2 corresponds to an integration time in the integrating amplifiers 50, which is set as an interval of sampling the dose detection signal. The first buffer memory 54a serves as the active buffer in the primary cycle, whereas the second buffer memory 54b serves as the active buffer in the secondary cycle. Note that the length T1 of the primary cycle may be equal to or shorter than the length T of the ordinary cycle if an adequate S/N ratio of the dose detection signal Sd could be achieved with that.

With regard to the Sd, the primary cycle consists of sampling and holding an analog dose detection signal S(N) in the CDS circuits 51, as shown in the timing chart "CDS" in FIG. 4, wherein the analog dose detection signal S(N) is based on charges s(N) from the detective pixels 65 having been integrated in the integrating amplifiers 50 during the preceding set of primary and secondary cycles; converting the analog dose detection signal S(N) through the A/D converter 53 to a digital dose detection signal Sd(N), as shown in the timing chart "AD DATA"; storing the Sd(N) temporarily in the buffer memory 54a; and simultaneously outputting the dummy signal Dd(N−1) from the buffer memory 54b to the memory 60, as shown in the timing chart "DATA OUT", wherein the Dd(N−1) has been temporarily stored in the buffer memory 54b in the preceding secondary cycle.

The following secondary cycle consists of sampling and holding an analog dummy signal D (N); converting the dummy signal D(N) to a digital dummy signal Dd(N); storing the Dd(N) temporarily in the buffer memory 54b; and simultaneously outputting the Sd(N−1), which has been temporarily stored in the buffer memory 54b in the preceding primary cycle, to the memory 60. This way, analog-to-digital conversion of the S(N), temporary storage or input of the Sd(N) in the buffer memory 54a, and the output of the Sd (N) from the buffer memory 54a to the memory 60 are accomplished in each set of primary and secondary cycles. In the dose detecting operation, the charges from the detective pixels 65 are read all at once at each sampling operation, so that the dose detection signal Sd read out from all detective pixels 65 will be recorded in the memory 60 in each set of primary and secondary cycles.

The dummy signal Dd is merely an expedient signal used for outputting the Sd from the buffer memory 54a as soon after the Sd has been written in the buffer memory 54a in the primary cycle as possible. That is, the Dd is not used for determining the start of x-ray radiation, but discarded after being output from the buffer memory 54b. The memory 60 accepts only the Sd from the buffer memory 54a in the secondary cycle, but rejects the Dd from the buffer memory 54b in the primary cycle.

As marked by a chain-dotted circle "A" in FIG. 4, the analog clock signal is applied at very shorter intervals in the secondary cycle than in the primary cycle, for the sake of cutting time for sampling and holding the dummy signal D. By setting the length T2 of the secondary cycle very shorter than the length T1 of the primary cycle (T1>>T2), the Sd will substantially be output to the memory 60 immediately after this signal is obtained through the analog-to-digital conversion.

Now the procedure for taking an x-ray image in the radiography system 2 will be described with reference to FIGS. 4, 5, 16 and 17.

First, the subject is positioned in front of the radiographic stand 15 or on top of the radiographic table 16, and the electronic cassette 13 mounted in the radiographic stand 15 or the radiographic table 16 is adjusted in vertical and horizontal positions to the position of the target site of the subject. Also the vertical and horizontal positions of the x-ray source 10 and the field of radiation from the x-ray source 10 are adjusted to the position of the electronic cassette 13 and the size of the target site. Next, the image acquisition settings are input in the source controller 11 and the console 14.

Figure 5:
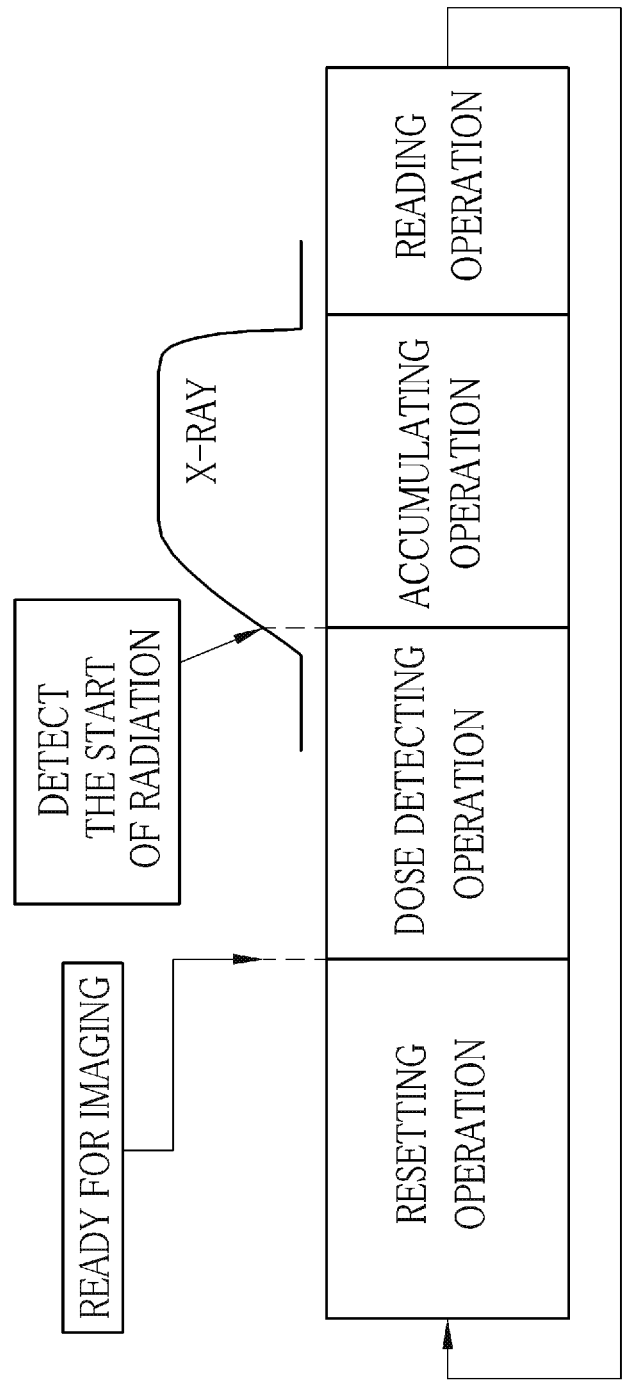
FIG. 5 is a chart illustrating the flow of operations for x-ray imaging of a flat panel detector in the electronic cassette.

Referring to FIG. 5, a sequence of operations in the FPD 35 is illustrated. Unless a standby instruction to prepare for imaging is sent from the console 14 to the electronic cassette 13, the controller 32 controls the FPD 35 to repeat the resetting operation. The standby instruction is sent from the console 14 to the electronic cassette 13 in response to an input operation by the operator, which should be done after the position of the electronic cassette 13 is adjusted to the subject and the image acquisition settings are input in the source controller 11. In response to the standby instruction, the controller 32 switches the FPD 35 from the resetting operation to the dose detecting operation. Then, charges generated in the detective pixels 65 flow through the signal lines 41 into the capacitors 50b of the integrating amplifiers 50. Since the TFTs 39 are turned off in the dose detecting operation, charges will be accumulated in the ordinary pixels 36. However, these charges will be discarded by the resetting operation immediately after the start of radiation is determined.

In the dose detecting operation, the signal processing circuit 43 repeats the pipeline processing in sets of one primary cycle and the following secondary cycle. In the primary cycle, the analog dose detection signal S based on charges from the detective pixels 65, which have been integrated in the integrating amplifiers 50 during the preceding set of primary and secondary cycles, are sampled and held in the CDS circuits 51; the analog dose detection signal S is converted through the A/D converter 53 to a digital dose detection signal Sd; and the Sd is temporarily stored in the buffer memory 54a. Simultaneously with the input of the Sd in the buffer memory 54a, the dummy signal Dd is output from the buffer memory 54b to the memory 60, but discarded as useless data. In the secondary cycle, the Sd is output from the buffer memory 54a to the memory 60. The Sd is then read out from the memory 60 to the start-of-radiation detector 61, to compare the maximum level of the Sd with the threshold level for determining the start of radiation.

When the operator pushes the activator switch 12 to trigger the x-ray source 10 to start radiating x-rays, the maximum level of the dose detection signal Sd will soon go above the threshold level. Then the start-of-radiation detector 61 determines the start of x-ray radiation, and outputs the radiation start detecting signal to the controller 32. Upon receipt of the radiation start detecting signal, the controller 32 drives the FPD 35 to make the resetting operation once and, thereafter, start the accumulating operation. Thus, the FPD 35 can start the accumulating operation synchronously with the start of x-ray radiation.

The controller 32 controls the FPD 35 to continue the accumulating operation for a certain time determined as one of the image acquisition settings and, thereafter, proceed to the reading operation for reading a frame of image data. In the reading operation, the signal processing circuit 43 conducts the pipeline processing in the same way as in the prior art shown in FIG. 16, so that the digital image signal Pd will be output alternately from the primary and secondary buffer memories 54a and 54b. After the reading operation, the FPD 35 returns to the resetting operation. The image data read into the memory 60 is subjected to various image renderings and then transmitted through the communicator 30 to the console 14, to be displayed as an x-ray image on the monitor 14b.

If the dose detecting operation would be conducted in constant cycles, like as shown in FIG. 17, the pipeline processing would be repeated in the primary cycles without executing the secondary cycles. Therefore, it would take the time T1 of one cycle from the input of the Sd in the buffer memory 54a or 54b to the output of the same dose detection signal Sd to the memory 60. Since the length T1 of the primary cycle is set several times to several-ten times longer than the constant cycle period T for the image reading, in order to achieve a sufficient S/N ratio of the dose detection signal Sd, the delay of one cycle period due to the prior art pipeline processing shown in FIG. 17 would get beyond ignorable range. In contrast to the prior art, the present embodiment using the secondary cycle speeds the output of the Sd from the buffer memory. Concretely, if the x-ray radiation starts actually at the same time as the integration amplifiers start integration, the delay time from the start of radiation till it is determined by the start-of-radiation detector 61 would be almost triple cycle periods in the prior art of FIG. 17, whereas the delay time would substantially be as short as double the cycle period in the present embodiment, because the length of the secondary cycle is extremely short. Thus, the start-of-radiation detector 61 can detect the start of x-ray radiation in a shorter time from the actual start thereof as compared to the prior art. As a result, the present embodiment can provide remarkable effects that unnecessary exposure of the subject to x-rays can be reduced and the radiated x-rays can be efficiently reflected on the x-ray image.

It is to be noted that the integrating amplifiers 50 may be reset at the end of each cycles although the integrating amplifiers 50 are not reset at the ends of the primary cycles, but only at the ends of the secondary cycles in the present embodiment. In that case, the integration time for the dose detection signal is equal to the length T1 of the primary cycle, and the charges "s" integrated throughout the length T1 in the primary cycle are read as an analog dose detection signal to the CDS circuits 51 at the end of the primary cycle, and the corresponding dose detection signal Sd is temporarily stored in the secondary buffer memory 54b during the secondary cycle following the primary cycle. Thereafter, the dose detection signal Sd is output from the buffer memory 54b to the memory 60 in the next primary cycle. On the other hand, the dummy signal is temporarily stored in the buffer memory 54a in the primary cycle, and is output from the buffer memory 54a to the memory 60 in the next secondary cycle.

[Second Embodiment]

Figure 6:
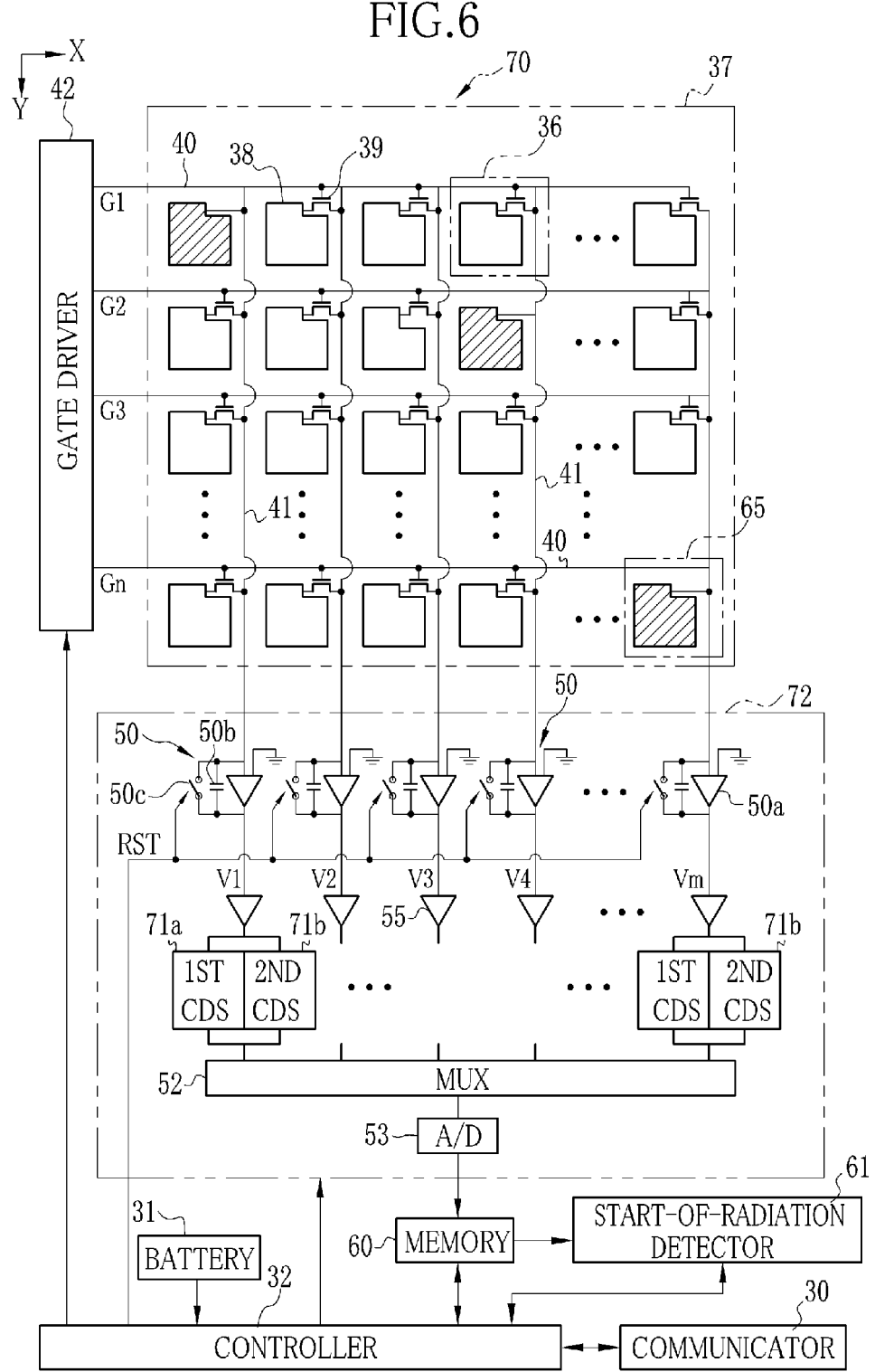
FIG. 6 is a block diagram illustrating an internal structure of an electronic cassette provided with a pair of CDS circuits at the output of each integrating amplifier.

In the above first embodiment, the first and second buffer memories 54a and 54b are provided as the signal holding devices for executing the pipeline processing. Alternatively, as shown in FIG. 6, an FPD 70 may use a signal processing circuit 72, wherein a pair of parallel-connected CDS circuits 71a and 71b is connected to the output of each integrating amplifier 50 individually through an amplifier 55, and the CDS circuit 71a and 71b function as the signal holding devices for pipeline processing.

Figure 7:
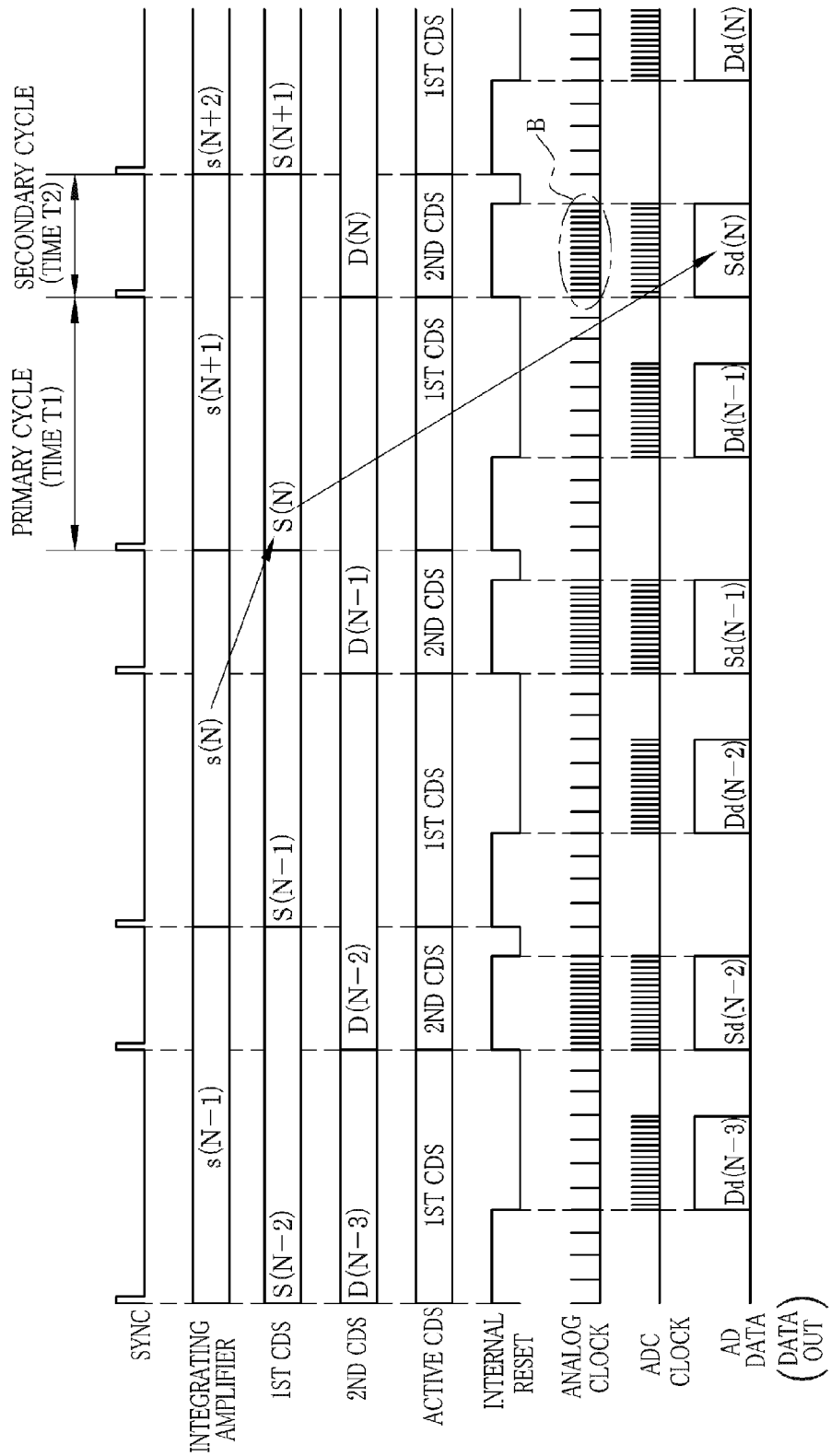
FIG. 7 shows timing charts of a dose detecting operation conducted by a pipeline-type signal processing circuit of the embodiment shown in FIG. 6.

The signal processing circuit 72 operates in the manner as shown in FIG. 7 for dose detecting operation. In FIG. 7, "Active CDS" indicates which of the first and second CDS circuits 71a and 71b is sampling and holding the dose detection signal S or the dummy signal D in the current cycle. In this example, the CDS circuits 71a starts sampling and holding the dose detection signal S in a primary cycle, whereas the CDS circuits 71b starts sampling and holding the dummy signal D in a secondary cycle (see the timing charts "$1^{st}$ CDS" and "$2^{nd}$ CDS").

As shown in FIG. 7, the signal processing circuit 72 of the present embodiment repeats the pipeline processing in sets of one primary cycle and the following secondary cycle, like the first embodiment. In the primary cycle, a dose detection signal S(N) based on charges s(N) integrated in the preceding set is sampled and held in the first CDS circuits 71a (see "1st CDS") and, at the same time, a dummy signal D(N−1) sampled and held in the second CDS circuits 71b in the preceding secondary cycle is converted through an A/D converter 53 and output to a memory 60 (see "AD Data"). Because no buffer memory is connected to the output of the A/D converter 53, and the A/D converter 53 is directly connected to the memory 60, the timing chart "AD Data" in the present embodiment corresponds to the timing chart "Data Out" in the first embodiment.

In the following secondary cycle, the dummy signal D(N) is being sampled and held in the second CDS circuits 71b and, at the same time, the dose detection signal S(N) sampled and held in the first CDS circuits 71a in the preceding primary cycle is converted to a digital dose detection signal Sd(N) and output to the memory 60. Like in the first embodiment, an analog clock signal for sampling and holding the dummy signal D in the second CDS circuits 71b is applied at shorter intervals in the secondary cycles, as marked by a chain-dotted circle B in the present embodiment, in order to cut the time taken for sampling and holding the dummy signal and hence reduce the length T2 of the secondary cycle. The present embodiment can provide the same effect as the first embodiment. Except that the CDS circuits are served for the pipeline processing in place of the buffer memories, the present embodiment may be configured in the same way as the first embodiment. Therefore, the description of the same structures and operations as the first embodiment will be omitted.

[Third Embodiment]

Figure 8:
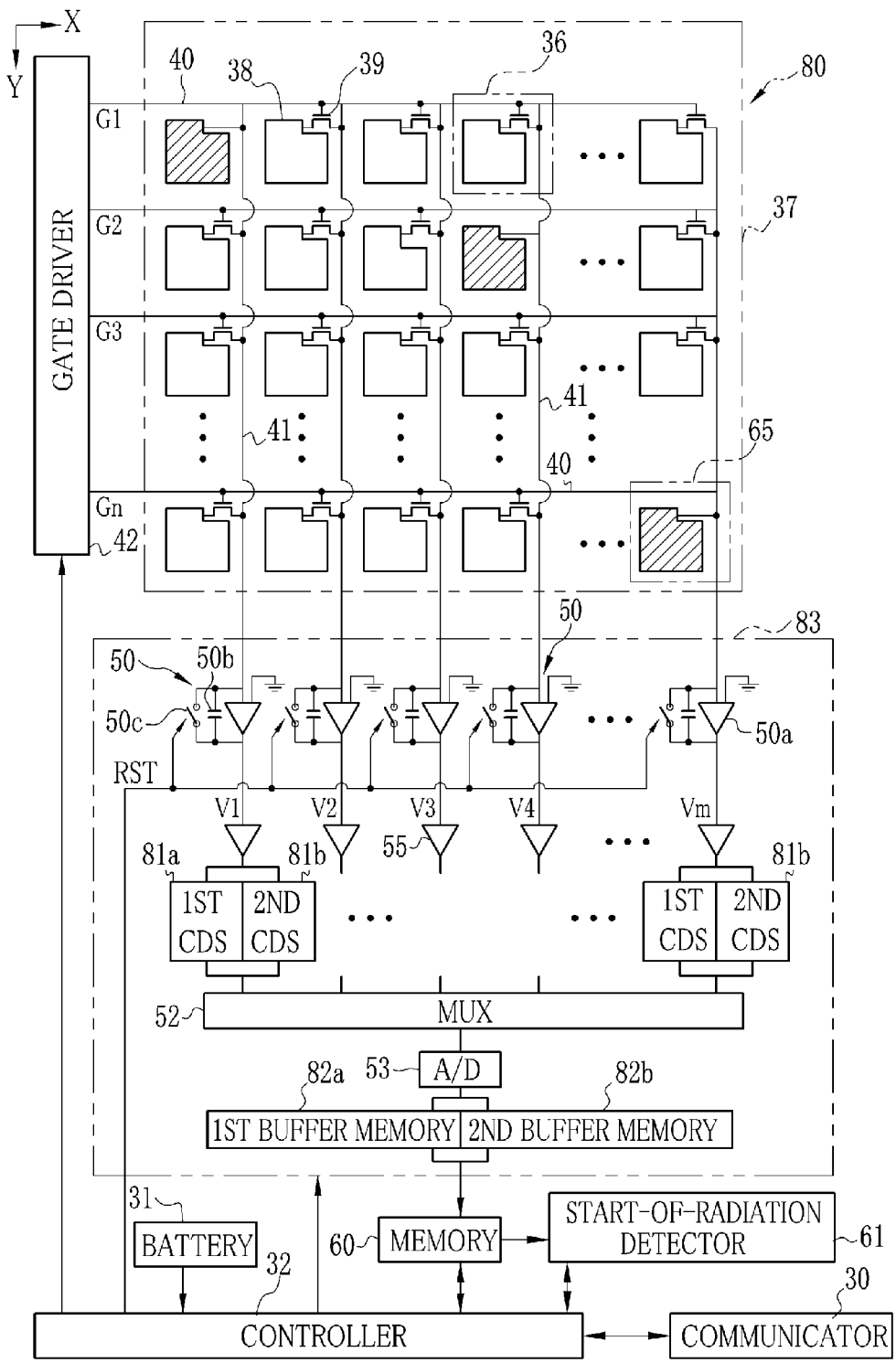
FIG. 8 is a block diagram illustrating an internal structure of an electronic cassette provided with a pair of CDS circuits at the output of each integrating amplifier, and first and second buffer memories.
Figure 9:
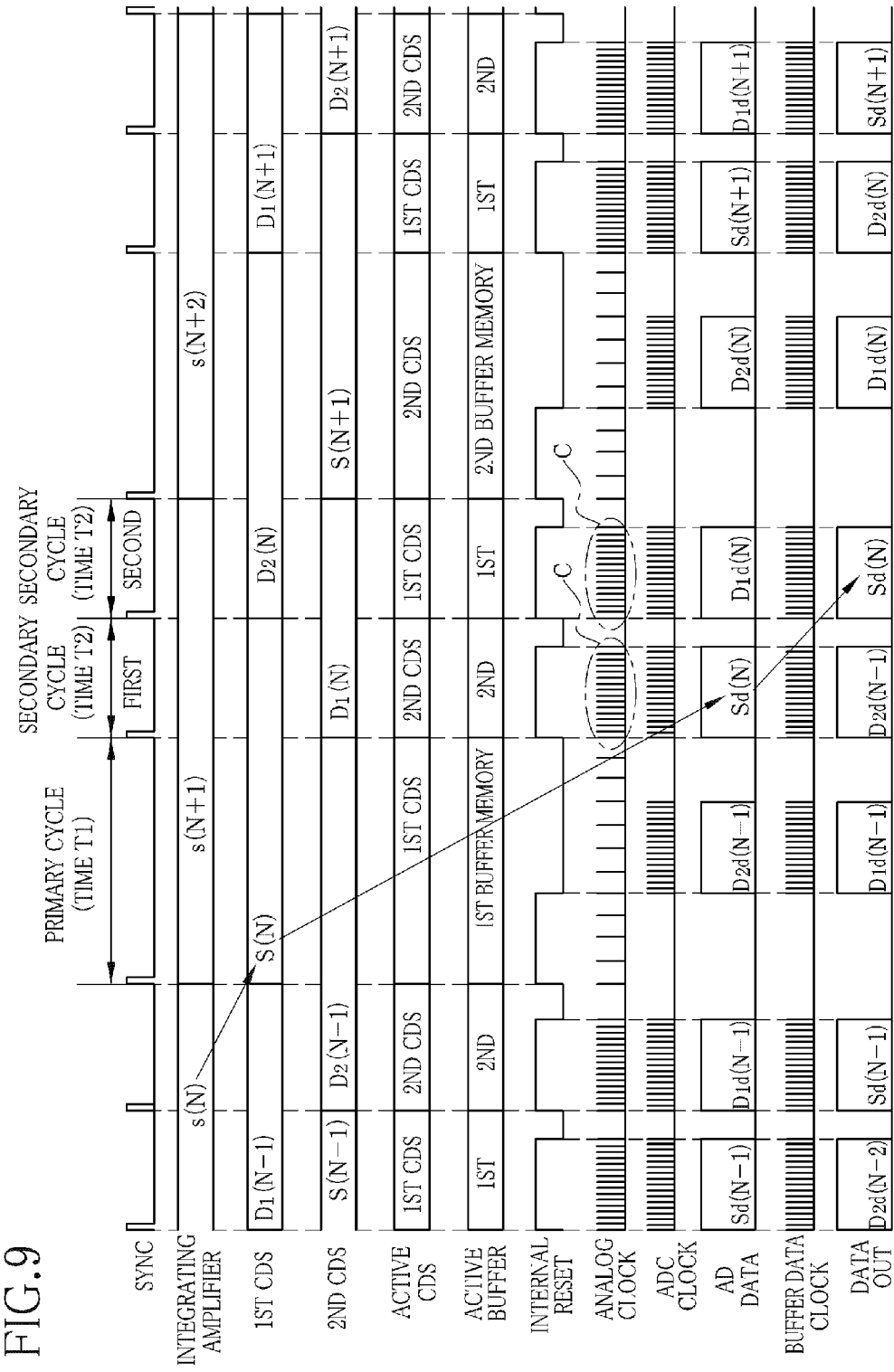
FIG. 9 shows timing charts of a dose detecting operation conducted by a pipeline-type signal processing circuit of the embodiment shown in FIG. 8.

Furthermore, the first and second embodiments may be combined into a third embodiment, as shown in FIG. 8, wherein a signal processing circuit 83 of a flat panel detector (FPD) 80 is provided with first and second CDS circuits 81a and 81b and first and second buffer memories 82a and 82b as signal holding devices. According to this embodiment, the signal processing circuit 83 operates for the dose detecting operation in a manner as shown in FIG. 9.

In the dose detecting operation, the signal processing circuit 83 repeats the pipeline processing in sets of a primary cycle and following two secondary cycles. In the primary cycle, a dose detection signal S(N) based on those charges s(N) which have been integrated by respective integrating amplifiers 50 in the preceding set are sampled and held in the first CDS circuits 81a (see the timing chart "1st CDS"); a dummy signal $D_2(N-1)$, which has been sampled and held in the second CDS circuits 81b in the latter secondary cycle, is converted through an A/D converter 53 to a digital dummy signal $D_2d(N-1)$ (see "AD Data"); and the dummy signal $D_2d(N-1)$ is temporarily stored in the first buffer memory 82a. Simultaneously, a dummy signal $D_1d(N-1)$, which have been temporarily stored in the second buffer memory 82b in the latter secondary cycle, is output from the second buffer memory 82b to a memory 60 (see "Data Out").

In the secondary cycle next to the primary cycle, a dummy signal $D_1(N)$ is sampled and held in the second CDS circuits 81b; the dose detection signal S(N), which have been sampled and held in the first CDS circuit 81a in the primary cycle, is converted to a digital dose detection signal Sd(N); the dose detection signal Sd(N) is temporarily stored in the second buffer memory 82b; and the dummy signal $D_2d(N-1)$, which is temporary stored in the first buffer memory 82a in the primary cycle, is output to the memory 60. These procedures are conducted simultaneously. In the succeeding secondary cycle, a dummy signal $D_2(N)$ is sampled and held in the first CDS circuits 81a; the dummy signal $D_1(N)$, which has been sampled and held in the second CDS circuits 81b in the preceding secondary cycle, is converted to a digital dummy signal $D_1d(N)$; the digital dummy signal $D_1d(N)$ is temporarily stored in the first buffer memory 82a; and the dose detection signal Sd(N), which has been temporarily stored in the second buffer memory 82b in the preceding secondary cycle, is output to the memory 60. These procedures are conducted simultaneously. Also in this embodiment, like the first and second embodiments, an analog clock signal is applied at shorter intervals in the secondary cycles, as marked by chain-dotted circles C. This way, the dose detection signals Sd will be output to the memory 60 at shorter intervals than conventional pipeline processing.

It is to be noted that the length of each secondary cycle in the first and second embodiments may be determined so as to ensure a sufficient time enough for outputting the dose detection signal Sd from the first buffer memory 54a to the memory 60 in the first embodiment, or a sufficient time enough for digitizing the dose detection signals S (N) being sampled and held in the first CDS circuits 71a in the second embodiment. Because the dummy signal Dd is not utilized for detecting the start of x-ray radiation, it is unnecessary to execute the sampling and holding and the analog-to-digital conversion of the analog dummy signal D in the secondary cycle as strictly as for the dose detection signal S in the primary cycle. Accordingly, for the shorter time T2 of secondary cycle, which is achieved by applying the analog clock signals at shorter intervals during the secondary cycle in the first and second embodiments, it may be possible to apply the analog clock signals at the same intervals as for the primary cycle but in a reduced number for the secondary cycle. In that case, the sampling and holding and the analog-to-digital conversion of the dummy signal D will safely be interrupted in the secondary cycle. It may also be possible not to apply the analog clock signal but only the synchronizing signal at shorter intervals in the secondary cycles, so that the sampling and holding and the analog-to-digital conversion of the dummy signal D will not substantially be carried out, but only the dose detection signal Sd will be output to the memory 60 in the secondary cycle. This will further shorten the time T2 of the secondary cycle, allowing more speedy output of the dose detection signal Sd.

Likewise, in the third embodiment, it is unnecessary to strictly conduct the outputting of the dummy signal Dd from the buffer memory in the former secondary cycle and the analog-to-digital conversion of the dummy signal D in the latter secondary cycle as well. Therefore, either of these processes may be cut short before the number of clocks of the buffer data clock signal or the ADC clock signal gets to the number set for the primary cycle respectively in the former secondary cycle or in the latter secondary cycle. Thus, the length of the secondary cycle can be more reduced. Concretely, the outputting of the dummy signal Dd from the buffer memory can be interrupted before the dummy signal Dd is completely read out from all memory cells of the buffer memory, or the analog-to-digital conversion of the dummy signal D can be interrupted before being done on all pixel columns or signal lines. Alternatively, these processes may be done on every second column or on every plural number "i" of successive columns while skipping a plural number "j" of following columns. Moreover, it may be possible not to apply the buffer data clock signal or the ADC clock signal in the secondary cycles, so as not to execute the reading of the dummy signal from the buffer memory or the analog-to-digital conversion of the dummy signal. Also the operation control signals may be applied to the MUX 52 at shorter intervals or in a reduced number, interrupting or thinning the operation control signals, in the secondary cycle as compared to the primary cycle. Alternatively, the operation control signals may not be output to the MUX 52 in the secondary cycle. The above-mentioned methods for cutting the time T2 of the secondary cycle, that is, shortening the intervals of the analog clocks, interrupting or thinning the selection of the sample-and-hold circuits by the MUX, canceling the analog-to-digital conversion of the dummy signal or the reading thereof from the buffer memory, may be adopted individually or in combination.

[Other Embodiments]

Figure 10:
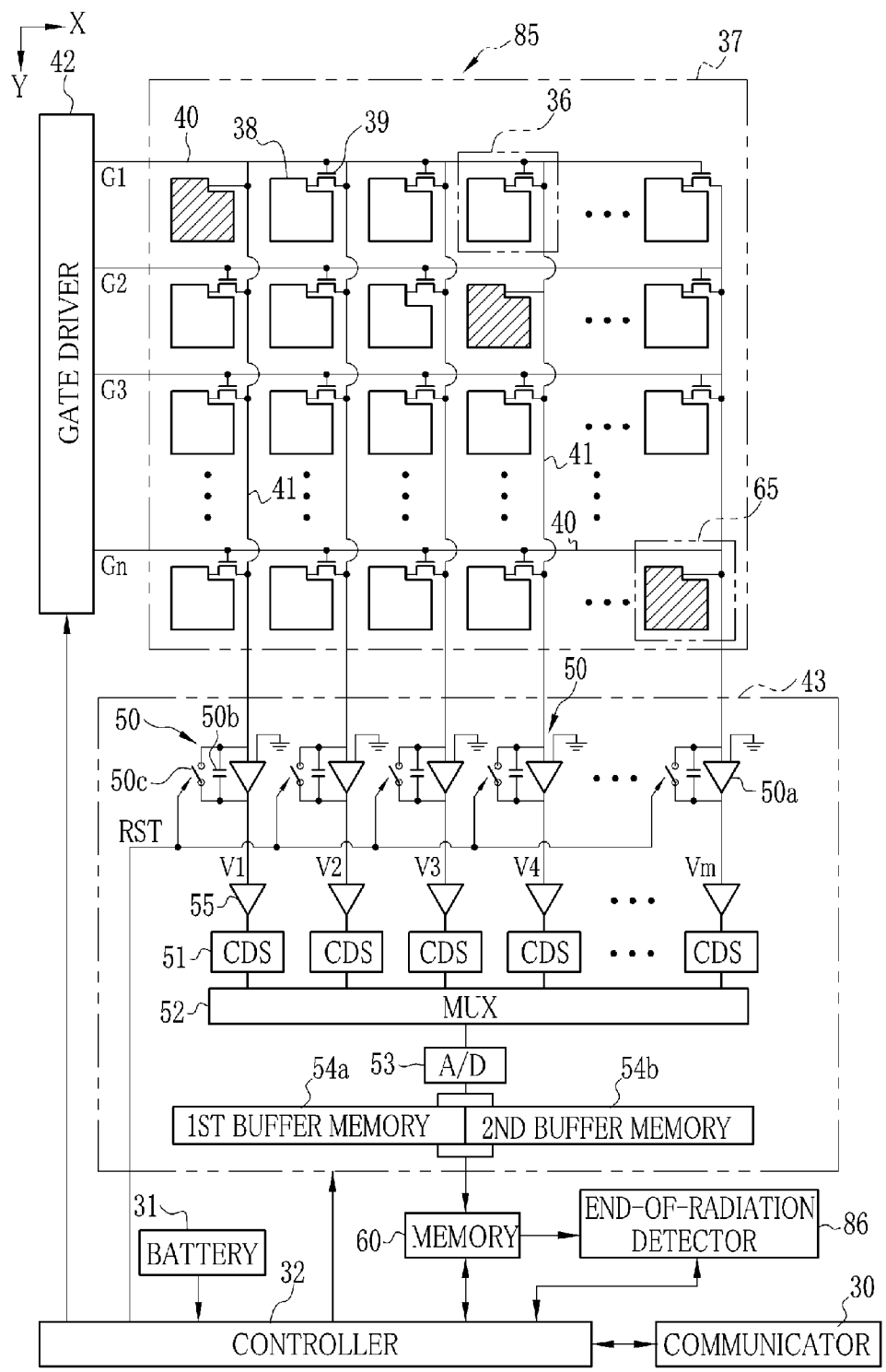
FIG. 10 is a block diagram illustrating an internal structure of an electronic cassette having an end-of-radiation detector.

Instead of detecting the start of x-ray radiation on the basis of the dose detection signal Sd, it is possible to detect the end of x-ray radiation on the basis of the dose detection signal Sd obtained through the dose detecting operation consisting of the primary cycles and the secondary cycles. In that case, as shown in FIG. 10, a flat panel detector (FPD) 85 is provided with an end-of-radiation detector 86 in place of the start-of-radiation detector 61. The end-of-radiation detector 86 compares the maximum level of the dose detection signal Sd with a threshold level for detecting the end of radiation, to determine that x-ray radiation is terminated when the maximum level goes below the threshold level for detecting the end of radiation. Upon the end of x-ray radiation being detected by the end-of-radiation detector 86, a controller 32 controls the FPD 85 to proceed from the accumulating operation to the reading operation. Note that the FPD 85 has the same structure as the FPD 35 of FIG. 3, except but the end-of-radiation detector 86 is provided in place of the start-of-radiation detector 61. Therefore, the description on the same components will be skipped here. It may be possible to provide both the start-of-radiation detector 61 and the end-of-radiation detector 86, to detect the start and end of x-ray radiation on the basis of the dose detection signal Sd.

Figure 11:
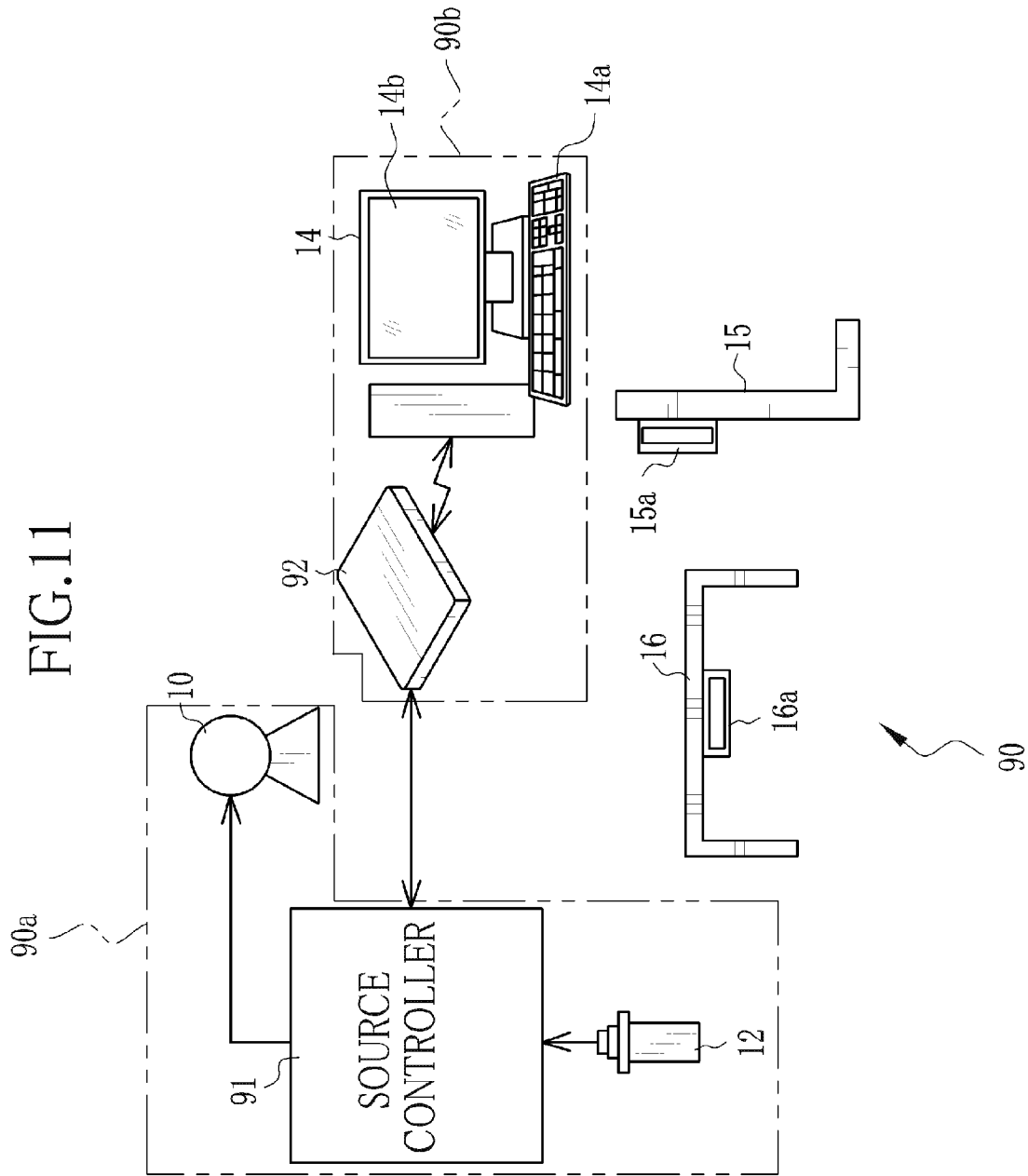
FIG. 11 is a schematic diagram illustrating a radiography system equipped with a communication device between a source controller and an electronic cassette.
Figure 12:
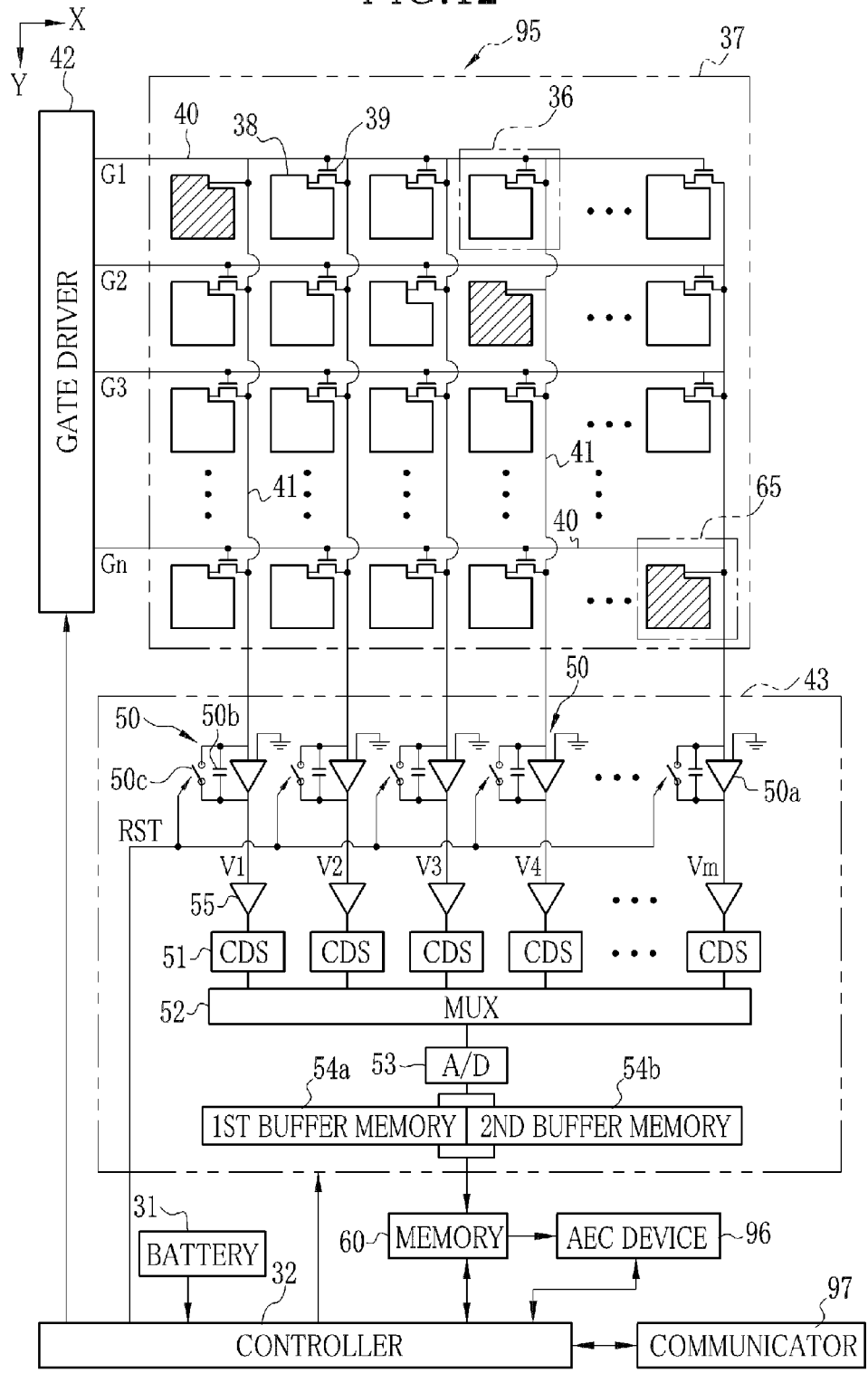
FIG. 12 is a block diagram illustrating an internal structure of an electronic cassette having an AEC device.

Moreover, the dose detection signal Sd may be used for automatic exposure control (AEC) in the following manner:

Referring to FIG. 11, a radiography system 90 is provided with a source controller 91 and an electronic cassette 92, which can exchange various synchronizing signals with each other. As shown in FIG. 12, a flat panel detector (FPD) 95 of the electronic cassette 92 is provided with an AEC device 96 in place of the start-of-radiation detector 61, and is able to communicate with a source controller 91 through a communicator 97. The communicator 97 also establishes the communication with a console 14, in the same way as the communicator 30. The radiography system 90 has the same structure and operates in the same way as the radiography system 2 of the embodiment of FIG. 1, except but the source controller 91 and the electronic cassette 92 are communicable with each other. Likewise, the FPD 95 is equivalent to the FPD 35 of FIG. 3 except but the FPD 95 is provided with the AEC device 96 in place of the start-of-radiation detector 61. Therefore, the description on the same components and functions as the first embodiment will be omitted here.

In this embodiment, the source controller 91 should set up the x-ray source 10 with a sufficient radiation time enough for preventing underexposure, which may be caused if the set radiation time is over before the AEC device 96 decides to stop the radiation from the x-ray source 10 as the cumulative amount of x-ray dose has reached a proper level. For this reason, the source controller 91 may preferably set up the radiation time at an upper safely limit that is allowed for each target site to be imaged. The source controller 91 controls the radiation according to the image acquisition settings, including the tube voltage, the tube current and the radiation time. On the other hand, the AEC function is to stop the radiation when the cumulative amount of dose has reached a proper requisite level, even before the radiation time set by the source controller 11 is over.

In addition, the console 14 stores information on one or more dose detection field within the FPD 95, in which the AEC device 96 measures the cumulative amount of dose, so that the information on the dose detection field is supplied to the electronic cassette 92 together with other image acquisition settings entered on the console 14. The dose detection field may correspond to an area-of-interest or may be located in a portion of an imaging area 37 where the dose detection signal Sd may be stably obtained. For example, if the chest is the target site to be imaged, the areas corresponding to right and left lungs are designated as the dose detection fields.

Figure 13:
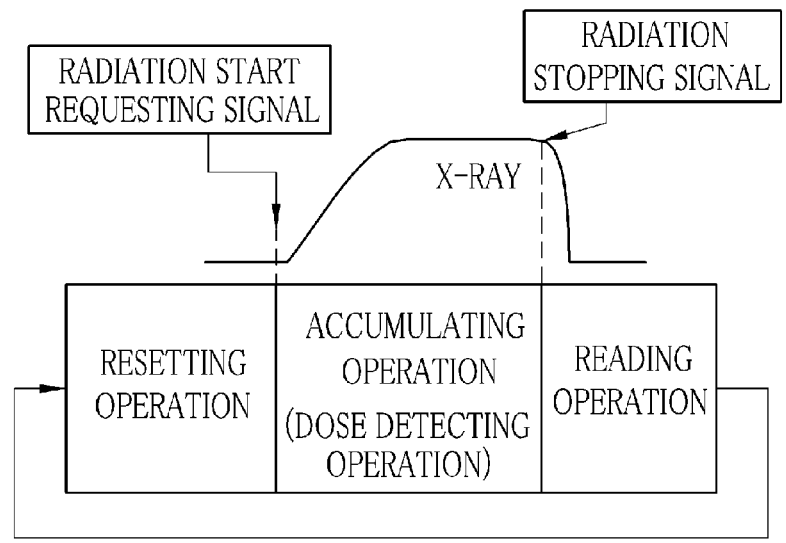
FIG. 13 is a chart illustrating the flow of operations for x-ray imaging of a FPD in the electronic cassette shown in FIGS. 11 and 12.

As shown in FIG. 13, upon receipt of a warm-up start signal from an activator switch 12, the source controller 91 sends a radiation start inquiry signal to the electronic cassette 92, the radiation start inquiry signal being a synchronizing signal for inquiring whether it is allowed to start x-ray radiation or not. When the electronic cassette 92 receives the radiation start inquiry signal at the communicator 97, the FPD 95 is controlled to stop the resetting operation and start the accumulating operation. Thereafter, a radiation start acknowledging signal is sent back from the communicator 97 to the source controller 91 in response to the radiation start inquiry signal. When the source controller 91 receives the radiation start acknowledging signal from the electronic cassette 92 and then receives a radiation starting signal from the activator switch 12, the source controller 91 controls the high-voltage generator to start power-supply to the x-ray source 10, causing the x-ray source 10 to radiate x-rays. Thereafter when the source controller 91 receives a radiation stopping signal, which is sent from the communicator 97, the source controller 91 stops the power-supply from the high-voltage generator to the x-ray source 10, ending x-ray radiation.

The AEC device 96 is actuated when the FPD 95 starts the accumulating operation. A signal processing circuit 43 of the FPD 95 also conducts the same dose detecting operation as in the first embodiment, periodically outputting the dose detection signal Sd to a memory 60.

The AEC device 96 measures the cumulative amount of x-ray dose onto the imaging area 37 by adding up the dose detection signals Sd, which are sequentially read out from the memory 60, on individual pixels which are located by the coordinate values in the memory 60. More specifically, the AEC device 96 calculates a representative value (mean value, maximum value, most-frequent value, sum or the like) of the dose detection signals Sd from those detective pixels 65 which exist in the dose detection field, on the basis of information on the dose detection field given from the console 14. Then the AEC device 96 integrates the representative values to determine the cumulative amount of dose onto the dose detection field.

The dose detection field may be determined otherwise. For example, the imaging area 37 may be divided into several blocks so that a representative value of the dose detection signal may be integrated in each block, to determine the one block providing the lowest integrated value as the dose detection field. Alternatively, the operator may designate an appropriate portion of the imaging area 37 as the dose detection field.

The AEC device 96 compares the cumulative amount of dose, which is measured from dose detection field, with a predetermined threshold level for stopping the radiation at each output of the dose detection signal Sd, to determine whether the cumulative amount of dose reaches the threshold level. When the cumulative amount of dose in the dose detection field gets above the threshold level, the AEC device 96 determines that the cumulative amount of dose has reached a designated or requisite level, and outputs a radiation stopping signal to the controller 32.

When the AEC device 96 determines that the cumulative amount of x-ray dose incident on the dose detection field has reached the designated level, and outputs the radiation stopping signal to the controller 32, the controller 32 transmits the radiation stopping signal through the communicator 97 to the source controller 91, upon which the x-ray source 10 stops x-ray radiation. Simultaneously, the controller 32 controls the FPD 95 to shift from the accumulating operation to the reading operation. After completing the reading operation, the FPD 95 returns to the resetting operation.

Alternatively, the AEC device 96 may predict a time, in which the cumulative amount of dose will reach the designated level, by calculation based on comparison of the integrated value of the dose detection signal Sd with a threshold level for stopping x-ray radiation. The AEC device 96 may output a radiation stopping signal to the source controller 91 when the predicted time is over, or may transmit the predicted time to the source controller 91. In the case where the predicted time is transmitted to the source controller 91, the source controller 91 measures the radiation time and stops radiation from the x-ray source 10 when the predicted time is over. The controller 32 controls the FPD 95 to shift from the accumulating operation to the reading operation when the predicted time is over.

Since the signal processing circuit 43 makes the dose detecting operation according to any one of the above embodiments, the dose detection signals Sd will be output at shorter intervals than conventional. Thus, the x-ray radiation can be stopped immediately after the x-ray dose has reached the designated level, achieving a particular effect that the subject will not be overexposed to x-rays due to a delay in stopping the radiation.

In addition to or instead of the above applications of the dose detection signals Sd: detecting the start or the end of x-ray radiation, or controlling the radiation time, the dose detection signals Sd may be used for adjusting the gain at the integrating amplifiers in the image reading operation. In this embodiment, as shown in FIG. 14, gain-adjustable integrating amplifiers 100 are used in place of the integrating amplifiers.

Figure 14:
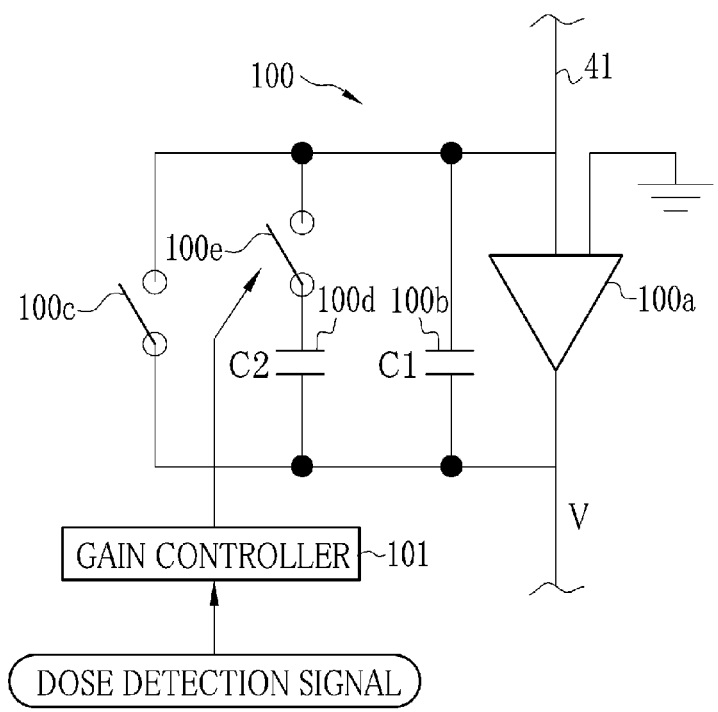
FIG. 14 is a block diagram illustrating an internal structure of an electronic cassette having a gain controller.

In FIG. 14, the integrating amplifier 100 is provided with an operational amplifier 100a and a reset switch 100c, like the integrating amplifier 50. However, two capacitors 100b and 100d are connected in parallel with the operational amplifier 100a, and a gain changing switch 100e is connected in serial to the capacitor 100d. Providing that "q" represents the accumulated charges, C1 and C2 represent respective capacitances of the capacitor 100b and 100d, a voltage signal V at the output of the integrating amplifier 100 equals q/(C1+C2); V=q/(C1+C2), while the gain changing switch 100e is on. While the gain changing switch 100e is off, the voltage V=q/C1. Turning the gain changing switch 100e on or off will change the gain at the integrating amplifier 100. Note that the number of capacitors connected to the operational amplifier 100a may preferably be more than two to make the gain changeable in more than two steps.

In the embodiment shown in FIG. 14, a gain controller 101 is provided in a flat panel detector (FPD), in place of or in addition to the start-of-radiation detector 61, the end-of-radiation detector 86 or the AEC device 96. The gain controller 101 is activated when the FPD starts the accumulating operation, and controls the gain changing switch 100e. In the same way as any of the above embodiments, a signal processing circuit makes the dose detecting operation to output the dose detection signals Sd at regular intervals to a memory. The gain controller 101 sets the gain at the integrating amplifiers 100 to be a minimum level in the dose detecting operation so that the dose detection signal Sd may not be saturated. In the present embodiment, the gain changing switch 100e is turned on in the dose detecting operation.

The gain controller 101 integrates a representative value of the dose detection signal from detective pixels 65 in a dose detection field, which corresponds to an area-of-interest in the imaging area 37, in the same way as the AEC device 96 does in the above embodiment, and compares the integrated value with a predetermined threshold level. If the integrated value is above the threshold level, the gain controller 101 turns on the gain changing switch 100e to set the gain at the integrating amplifiers 100 low in the image reading operation. On the other hand, if the cumulative amount of dose in the dose detection field is so low that the integrated value of the dose detection signal is below the threshold level, the gain controller 101 turns off the changing switch 100e to set the gain at the integrating amplifiers 100 higher in the image reading operation. More specifically, the gain at the integrating amplifiers 100 is adjusted so that the maximum and minimum values of the voltage signal V obtained from the dose detection field will correspond to the maximum and minimum values of the dynamic range of analog-to-digital conversion, respectively.

If the cumulative amount of dose is designated to be low for imaging, the range of maximum to minimum values of the voltage signal V can become so narrower than the dynamic range of analog-to-digital conversion that the obtained x-ray image has a bad resolution or suffers remarkable noises. By setting the gain at the integrating amplifiers higher when the detected cumulative amount of dose on the dose detection field is low, a good-quality x-ray image with fewer noises will advantageously be obtained.

Since the signal processing circuit makes the dose detecting operation according to any of the above embodiments and outputs the dose detection signals Sd at shorter intervals than conventional, it is possible to control the gain at the integrating amplifiers even while an extremely short exposure time, such as within several micro seconds, is designated and hence the FPD must terminate the accumulating operation in the extremely short time and switch to the image reading operation.

Note that the gain at the amplifiers 55 may be adjusted instead of the gain at the integrating amplifiers. Moreover, the gain control may be executed in combination with the detection of the start of radiation, the detection of the end of radiation and/or the automatic exposure control.

Figure 15:
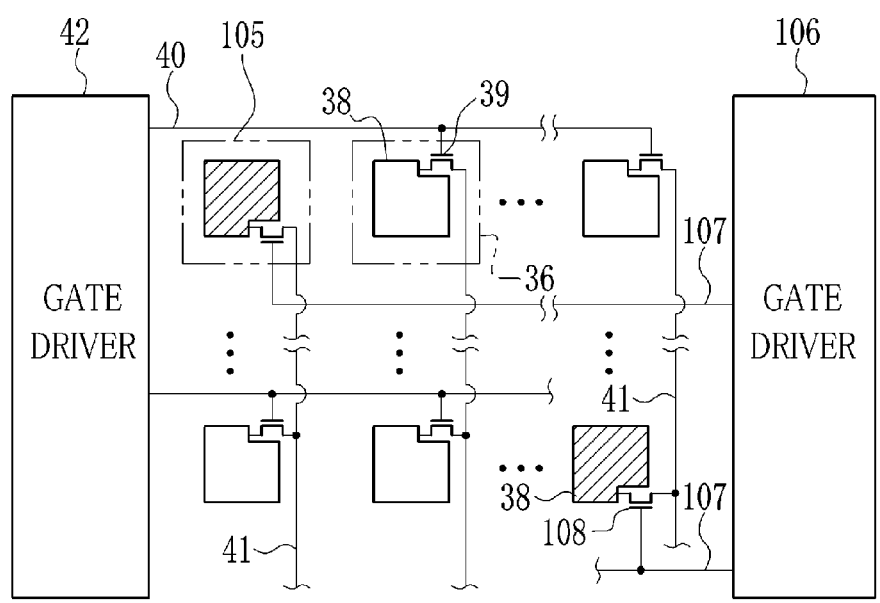
FIG. 15 is a block diagram illustrating another example of detective pixel.

In the above embodiments, the dose sensor is constituted of those detective pixels 65 which are directly connected to the signal lines 41 without any intermediate TFT 39. Instead of this configuration, it is possible to short-circuit the source of the TFT 39 to the drain thereof in some pixels 36 to serve these pixels as detective pixels. In an alternative, as shown in FIG. 15, detective pixels 105 may be connected to the signal lines 41 through such TFTs 108 that are connected to different scanning lines 107 and driven by a different gate driver 106 from those used for ordinary pixels 36, so that electric charges accumulated in these detective pixels 105 may be read out independently of the ordinary pixels 36. According to this embodiment, the gate driver 106 may selectively apply gate pulses to those detective pixels 105 which are located in a dose detection field, so as to read the accumulated charges from the detective pixels 105 in the dose detection field.

It is alternatively possible to read a dose detection signal through a signal processing circuit on the basis of leak charges which will leak from the pixels 36 while the TFTs 39 are off. In this embodiment, all pixels 36 serve as the dose detecting sensor. Instead of modifying the ordinary pixels to the detective pixels, it is possible to provide specific elements of a dose detecting sensor in between the ordinary pixels, and read the output of these elements of the dose detecting sensor through a signal processing circuit in accordance with the present invention. Namely, insofar as the dose detection signals are output through a pipeline-type signal processing circuit, the present invention is applicable to any type of radiographic image detector, to achieve the same effects as described with respect to the above embodiments.

While the console 14 and the electronic cassette 13 have been described as separate units in the above embodiments, the console 14 is not necessarily an independent unit, but the function of the console 14 may be incorporated into the electronic cassette 13. Moreover, the present invention is applicable not only to portable x-ray image detectors like the electronic cassette, but also to stationary radiographic image detectors which are individually integrated into radiographic stands or tables.

The present invention is applicable not only to x-ray radiography systems but also to radiography systems using other kinds of radioactive rays like gamma-rays.

It should be understood that the embodiments of the present invention have been described for illustrative purposes only. Those skilled in the art will appreciate that various modifications, additions and substitutions are possible without departing from the scope and spirit of the invention as disclosed in the accompanying claims.

What is claimed is:

1. A radiographic image detector for detecting radiographic images of a subject, comprising:
    a flat panel detector having an imaging area in which a plurality of columns of pixels for accumulating electric charges corresponding to the amounts of radioactive rays incident on the pixels, a dose sensor generating electric charges corresponding to the amount of radiated radioactive rays radiated from a radiation source, and signal lines provided for respective columns of the pixels are arranged in an array, wherein the pixels and the dose sensor are connected to the signal lines to output the electric charges accumulated in the pixels as image signals and the electric charges generated from the dose sensor as a dose detection signal through the signal lines;
    a pipeline-type signal processing circuit comprising a plurality of integrating amplifiers provided for the respective signal lines, to integrate and convert electric charges to voltage signals, and first and second signal holding devices for temporarily holding two sets of voltage signal as successively read out from the integrating amplifiers, wherein a set of voltage signal is being input to one of the first and second signal holding devices while a preceding set of voltage signal is being output from the other of the first and second signal holding devices;
    a memory for storing the image signal and the dose detection signal as voltage signals output from the signal processing circuit; and
    a controller for controlling operation timings of the flat panel detector, the signal processing circuit and the memory,
    wherein the controller controls the signal input and output of the first and second signal holding devices to be repeated in ordinary cycles of a constant length, which corresponds to an integrating session from a start of integration of electric charges till resetting the integrating amplifiers, in a reading operation for outputting the image signal to the memory,
    whereas the controller controls the signal input and output of the first and second signal holding devices to be repeated in two kinds of cycles, including primary cycles and secondary cycles of a shorter length than the primary cycles, in such a manner that at least one secondary cycle is conducted in between two primary cycles in a dose detecting operation for outputting the dose detection signal to the memory.

2. The radiographic image detector as claimed in claim 1, wherein the dose detection signal is used for at least one of determination of whether the radiation source has started radiation, determination of whether the radiation source has stopped radiation, automatic control of radiographic exposure, and gain control on the image signal in the reading operation.

3. The radiographic image detector as claimed in claim 1, wherein each of the integrating amplifiers integrates electric charges of one pixel per one signal line to output the image signal for one line in each ordinary cycle.

4. The radiographic image detector as claimed in claim 1, wherein the dose sensor comprises a plurality of elements dispersed over the imaging area, the integrating amplifiers integrate electric charges from the plurality of elements of the dose sensor all at once in the primary cycle and in the secondary cycle.

5. The radiographic image detector as claimed in claim 1, the primary cycle is longer than the ordinary cycle.

6. The radiographic image detector as claimed in claim 1, wherein, in the dose detecting operation, among of the two sets of voltage signal as being successively read out from the integrating amplifiers, only one set of voltage signal which is input in the first signal holding device or the second signal holding device is treated as the dose detection signal, and the other set of voltage signal is not treated as the dose detection signal but as a dummy signal containing useless data.

7. The radiographic image detector as claimed in claim 1, wherein one integrating session of the integrating amplifiers, which is set for the dose detecting operation, is divided between the primary cycle and the secondary cycle.

8. The radiographic image detector as claimed in claim 1, wherein one integrating session of a corresponding length is allotted to each of the primary and secondary cycles.

9. The radiographic image detector as claimed in claim 1, wherein the signal processing circuit further comprises CDS circuits connected to respective outputs of the integrating amplifiers, to sample and hold an analog voltage signal from the integrating amplifiers; and an A/D converter for converting the analog voltage signal sampled and held in the CDS circuits to a digital voltage signal.

10. The radiographic image detector as claimed in claim 9, the first and second signal holding devices are two buffer memories connected in parallel with each other in between the A/D converter and the memory.

11. The radiographic image detector as claimed in claim 9, wherein the CDS circuits are connected in pairs to the respective outputs of the integrating amplifiers, the CDS circuits of each pair being connected in parallel with each other to constitute the first and second signal holding devices respectively.

12. The radiographic image detector as claimed in claim 1, wherein the controller conducts the primary cycles and the secondary cycles alternately.

13. The radiographic image detector as claimed in claim 9, wherein one and the other of a pair of buffer memories, which are connected in parallel with each other in between the A/D converter and the memory, and one and the other of a pair of the CDS circuits, which are connected in parallel with each other to the output of each integrating amplifier, constitute the first signal holding devices and the second signal holding devices, respectively.

14. The radiographic image detector as claimed in claim 13, wherein the controller conducts two secondary cycles in between two primary cycles.

15. The radiographic image detector as claimed in claim 1, wherein the controller cuts the length of the secondary cycle shorter than the primary cycle by controlling the numbers or intervals of operation control signals applied to the signal processing circuit.

16. The radiographic image detector as claimed in claim 1, wherein some of the pixels serve as the dose sensor.

17. The radiographic image detector as claimed in claim 16, wherein the pixels include ordinary pixels that accumulate signal charges responding to radioactive rays and output the signal charges to the signal lines upon switching elements being turned on, and detective pixels connected directly to the signal lines without intermediate switching elements, the detective pixels serving as the dose sensor.

18. The radiographic image detector as claimed in claim 16, wherein the pixels include ordinary pixels that accumulate signal charges responding to radioactive rays and output the signal charges to the signal lines upon switching elements being turned on, and detective pixels provided with such switching elements that are driven independently of the switching elements of the ordinary pixels, the detective pixels serving as the dose sensor.

19. The radiographic image detector as claimed in claim 1, wherein the radiographic image detector is an electronic cassette containing the flat panel detector in a portable housing.

20. A method of operating a radiographic image detector for detecting radiographic images of a subject, the radiographic image detector comprising:
a flat panel detector having an imaging area in which a plurality of columns of pixels for accumulating electric charges corresponding to the amounts of radioactive rays incident on the pixels, a dose sensor generating electric charges corresponding to the amount of radiated radioactive rays radiated from a radiation source, and signal lines provided for respective columns of the pixels are arranged in an array, wherein the pixels and the dose sensor are connected to the signal lines to output the electric charges accumulated in the pixels as image signals and the electric charges generated from the dose sensor as a dose detection signal through the signal lines;
a pipeline-type signal processing circuit comprising a plurality of integrating amplifiers provided for the respective signal lines, to integrate and convert electric charges to voltage signals, and first and second signal holding devices for temporarily holding two sets of voltage signal as successively read out from the integrating amplifiers, wherein a set of voltage signal is being input to one of the first and second signal holding devices while a preceding set of voltage signal is being output from the other of the first and second signal holding devices;
a memory for storing the image signal and the dose detection signal as voltage signals output from the signal processing circuit; and
a controller for controlling operation timings of the flat panel detector, the signal processing circuit and the memory, wherein the method comprising the steps of:
making the controller, in a reading operation for outputting the image signal to the memory, control the signal input and output of the first and second signal holding devices to be repeated in ordinary cycles of a constant length corresponding to an integrating session from the start of integration of electric charges to resetting the integrating amplifiers; and
making the controller, in a dose detecting operation for outputting the dose detection signal to the memory, control the signal input and output of the first and second signal holding devices to be repeated in two kinds of cycles, including primary cycles and secondary cycles of a shorter length than the primary cycles, in such a manner that at least one secondary cycle is conducted in between the $(N-1)^{th}$ primary cycle and the $N^{th}$ primary cycle.

* * * * *